US009662093B2

(12) United States Patent
Nakatsuji

(10) Patent No.: US 9,662,093 B2
(45) Date of Patent: May 30, 2017

(54) ULTRASOUND OBSERVATION APPARATUS, METHOD FOR OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Tomohiro Nakatsuji, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/222,118

(22) Filed: Jul. 28, 2016

(65) Prior Publication Data

US 2016/0331348 A1 Nov. 17, 2016

Related U.S. Application Data

(63) Continuation of application No. PCT/JP2015/078547, filed on Oct. 7, 2015.

(30) Foreign Application Priority Data

Dec. 22, 2014 (JP) ................. 2014-259473

(51) Int. Cl.
 *A61B 8/08* (2006.01)
 *A61B 8/00* (2006.01)
 (Continued)

(52) U.S. Cl.
 CPC .............. *A61B 8/5207* (2013.01); *A61B 8/08* (2013.01); *A61B 8/12* (2013.01); *A61B 8/4444* (2013.01);
 (Continued)

(58) Field of Classification Search
 CPC ....... A61B 8/5207; A61B 8/08; A61B 8/4444; A61B 8/4483
 See application file for complete search history.

(56) References Cited

U.S. PATENT DOCUMENTS

2013/0035594 A1   2/2013 Eda
2014/0150556 A1*  6/2014 Angelsen ............ G01S 7/52095
                                            73/627

FOREIGN PATENT DOCUMENTS

JP      2013-166059 A      8/2013
WO   WO 2012/011414 A1    1/2012

OTHER PUBLICATIONS

International Search Report dated Dec. 22, 2015 issued in PCT/JP2015/078547.

* cited by examiner

*Primary Examiner* — Bo J Peng
(74) *Attorney, Agent, or Firm* — Scully, Scott, Murphy & Presser, P.C.

(57) ABSTRACT

An ultrasound observation apparatus for generating an ultrasound image based on an ultrasound signal obtained by an ultrasound probe having an ultrasound transducer for transmitting an ultrasound wave to an observation target and receiving the ultrasound wave reflected from the observation target. The ultrasound observation apparatus includes: a frequency analysis unit that analyzes a frequency of the ultrasound signal to calculate frequency spectra depending on a reception depth and a reception direction of the ultrasound signal; a frequency band setting unit that sets a frequency band used for calculating a feature of each of the frequency spectra by use of parameters associated with a frequency spectrum in each of candidate bands having different bandwidths; a feature calculation unit that calculates the feature of each of the frequency spectra based on the frequency band; and a feature image data generation unit that generates feature image data based on the feature.

9 Claims, 14 Drawing Sheets

(51) Int. Cl.
*A61B 8/12* (2006.01)
*G06T 7/00* (2017.01)

(52) U.S. Cl.
CPC .......... *A61B 8/4483* (2013.01); *A61B 8/5246* (2013.01); *A61B 8/5269* (2013.01); *A61B 8/5284* (2013.01); *A61B 8/54* (2013.01); *G06T 7/00* (2013.01); *A61B 8/0891* (2013.01)

ULTRASOUND OBSERVATION APPARATUS, METHOD FOR OPERATING ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2015/078547, filed on Oct. 7, 2015 which designates the United States, incorporated herein by reference, and which claims the benefit of priority from Japanese Patent Application No. 2014-259473, filed on Dec. 22, 2014, incorporated herein by reference.

BACKGROUND

1. Technical Field

The disclosure relates to an ultrasound observation apparatus for observing tissues as an observation target by use of ultrasound waves. The disclosure also relates to a method for operating the ultrasound observation apparatus, and a computer-readable recording medium.

2. Related Art

There has been conventionally known a technique for calculating a feature of a frequency spectrum of an ultrasound signal having a property depending on tissue characteristics and generating a feature image for distinguishing the tissue characteristics based on the feature in an ultrasound observation apparatus for observing tissues as an observation target by use of ultrasound waves (see WO 2012/011414 A, for example). With the technique, a frequency of a received ultrasound signal is analyzed thereby to obtain a frequency spectrum, and then an approximate equation of the frequency spectrum in a predetermined frequency band is calculated thereby to extract a feature based on the approximate equation.

SUMMARY

In some embodiments, an ultrasound observation apparatus is configured to generate an ultrasound image based on an ultrasound signal obtained by an ultrasound probe, the ultrasound probe having an ultrasound transducer for transmitting an ultrasound wave to an observation target and receiving the ultrasound wave reflected from the observation target. The ultrasound observation apparatus includes: a frequency analysis unit configured to analyze a frequency of the ultrasound signal to calculate a plurality of frequency spectra depending on a reception depth and a reception direction of the ultrasound signal; a frequency band setting unit configured to set a frequency band used for calculating a feature of each of the frequency spectra calculated by the frequency analysis unit by use of parameters associated with a frequency spectrum in each of a plurality of candidate bands having different bandwidths; a feature calculation unit configured to calculate the feature of each of the frequency spectra based on the frequency band set by the frequency band setting unit; and a feature image data generation unit configured to generate feature image data for displaying information on the feature calculated by the feature calculation unit. The frequency band setting unit includes: an envelope curve detection unit configured to detect an envelope curve of each of the frequency spectra; a parameter extraction unit configured to extract the parameters in the plurality of candidate bands, respectively, the parameters being associated with an approximate line obtained by approximating the envelope curve; a variation calculation unit configured to calculate a variation between two parameters respectively extracted in two candidate bands of the plurality of candidate bands having a predetermined relationship, among the parameters extracted per candidate band by the parameter extraction unit; and a determination unit configured to determine the frequency band based on the variation calculated by the variation calculation unit.

In some embodiments, a method for operating an ultrasound observation apparatus is provided. The ultrasound observation apparatus is configured to generate an ultrasound image based on an ultrasound signal obtained by an ultrasound probe, the ultrasound probe having an ultrasound transducer for transmitting an ultrasound wave to an observation target and receiving the ultrasound wave reflected from the observation target. The method includes: by a frequency analysis unit, analyzing a frequency of the ultrasound signal to calculate a plurality of frequency spectra depending on a reception depth and a reception direction of the ultrasound signal; by a frequency band setting unit, setting a frequency band used for calculating a feature of each of the frequency spectra by use of parameters associated with a frequency spectrum in each of a plurality of candidate bands having different bandwidths; by a feature calculation unit, calculating the feature of each of the frequency spectra based on the frequency band; and by a feature image data generation unit, generating feature image data based on the feature. The setting of the frequency band includes: by an envelope curve detection unit, detecting an envelope curve of each of the frequency spectra; by a parameter extraction unit, extracting the parameters in the plurality of candidate bands, respectively, the parameters being associated with an approximate line obtained by approximating the envelope curve; by a variation calculation unit, calculating a variation between two parameters respectively extracted in two candidate bands of the plurality of candidate bands having a predetermined relationship, among the parameters extracted per candidate band; and by a determination unit, determining the frequency band based on the variation.

In some embodiments, a non-transitory computer-readable recording medium with an executable program stored thereon is provided. The program causes an ultrasound observation apparatus that is configured to generate an ultrasound image based on an ultrasound signal obtained by an ultrasound probe, the ultrasound probe having an ultrasound transducer for transmitting an ultrasound wave to an observation target and receiving the ultrasound wave reflected from the observation target, to execute: by a frequency analysis unit, analyzing a frequency of the ultrasound signal to calculate a plurality of frequency spectra depending on a reception depth and a reception direction of the ultrasound signal; by a frequency band setting unit, setting a frequency band used for calculating a feature of each of the frequency spectra by use of parameters associated with a frequency spectrum in each of a plurality of candidate bands having different bandwidths; by a feature calculation unit, calculating the feature of each of the frequency spectra based on the frequency band; and by a feature image data generation unit, generating feature image data based on the feature. The setting of the frequency band includes: by an envelope curve detection unit, detecting an envelope curve of each of the frequency spectra; by a parameter extraction unit, extracting the parameters in the plurality of candidate bands, respectively, the parameters being associated with an approximate line obtained by approximating the envelope curve; by a variation calculation unit, calculating a variation between two parameters respectively extracted in two candidate bands of the plurality of candidate bands having a predetermined relationship, among the parameters extracted per candidate band; and by a determination unit, determining the frequency band based on the variation.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the accompanying drawings.

First Embodiment

Figure 1:
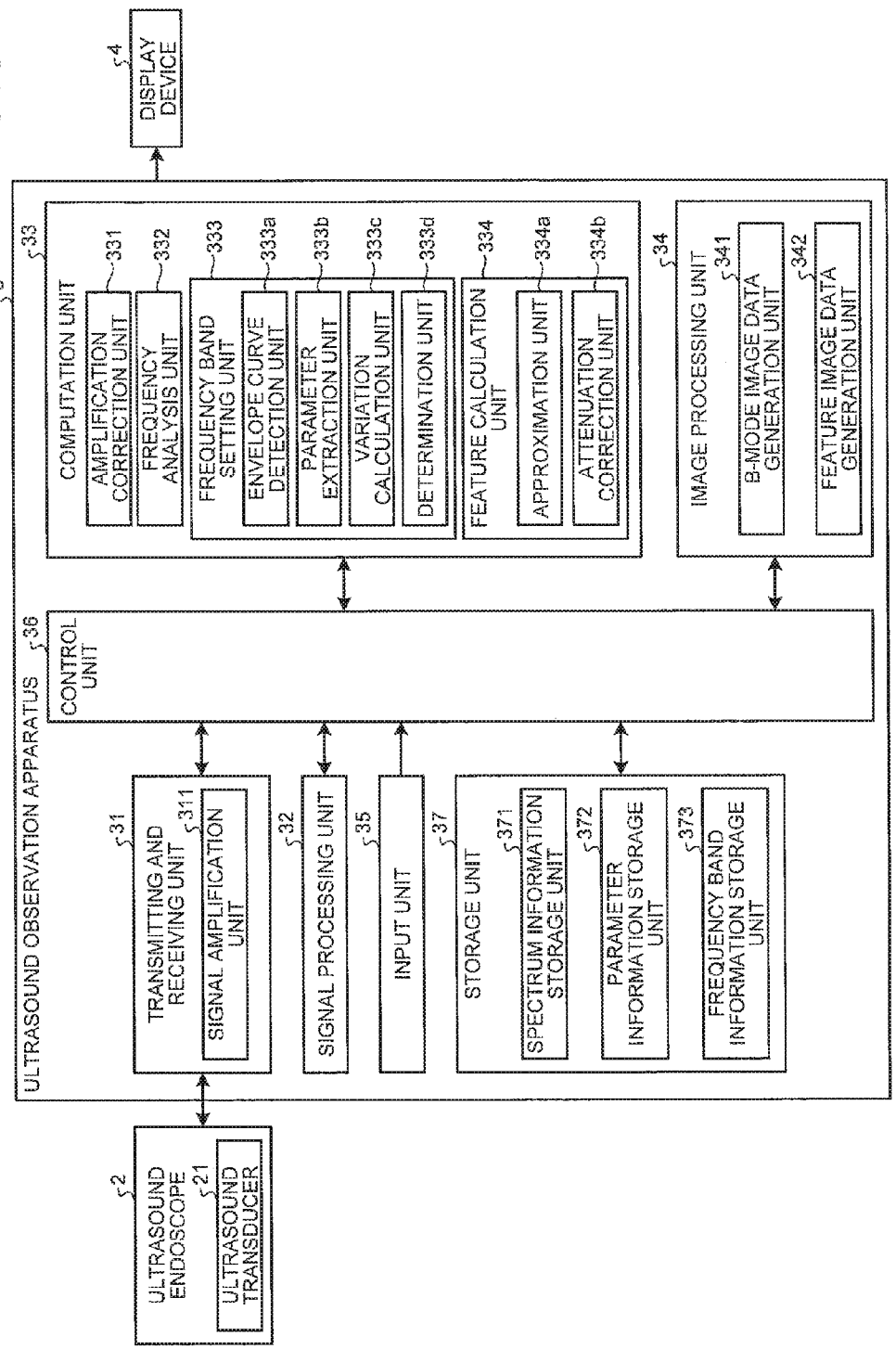
FIG. 1 is a block diagram illustrating a functional structure of an ultrasound diagnosis system including an ultrasound observation, apparatus according to a first embodiment of the present invention.

FIG. 1 is a block diagram illustrating a functional structure of an ultrasound diagnosis system including an ultrasound observation apparatus according to a first embodiment of the present invention. The illustrated ultrasound diagnosis system 1 includes an ultrasound endoscope 2 for transmitting an ultrasound wave to a subject as an observation target and receiving an ultrasound wave reflected by the subject, an ultrasound observation apparatus 3 for generating an ultrasound image based on the ultrasound signal obtained by the ultrasound endoscope 2, and a display device 4 for displaying the ultrasound image generated by the ultrasound observation apparatus 3.

The ultrasound endoscope 2 at the distal end has an ultrasound transducer 21 for converting an electric pulse signal received from the ultrasound observation apparatus 3 into an ultrasound pulse (acoustic pulse) and irradiating a subject with the ultrasound pulse, and converting an ultrasound echo reflected by the subject into an electric echo signal expressed by voltage change and outputting the electric echo signal. The ultrasound transducer 21 may be any of convex transducer, linear transducer, and radial transducer. The ultrasound endoscope 2 may cause the ultrasound transducer 21 to mechanically scan, or may cause the ultrasound transducer 21 to electronically scan by providing a plurality of devices in an array shape as the ultrasound transducer 21, and electronically switching the devices for transmission or reception or delaying transmission or reception of each device.

The ultrasound endoscope 2 generally has an imaging optical system and an imaging device, and is configured to be inserted into a digestive tract (esophagus, stomach, duodenum, or large bowel) or an organ of respiration (traches or bronchus) of a subject thereby to image a digestive tract, an organ of respiration, or its surrounding organ. (such as pancreas, gallbladder, bile duct, biliary tract, lymph nodes, mediastinal organ, and blood vessel). Further, the ultrasound endoscope 2 has a light guide for guiding an illumination light with which a subject is irradiated during imaging. The light guide is such that its distal end reaches the distal end of the insertion portion of the ultrasound endoscope 2 into a subject while its proximal end is connected to a light source device for generating an illumination light.

The ultrasound observation apparatus 3 includes a transmitting and receiving unit 31, electrically connected to the ultrasound endoscope 2, for transmitting a transmission signal (pulse signal) made of high-voltage pulses based on a predetermined waveform and a transmission timing to the ultrasound transducer 21 and receiving an echo signal as electric reception signal from the ultrasound transducer 21 thereby to generate and output data of a digital RF (Radio Frequency) signal (which will be denoted as RF data below), a signal processing unit 32 for generating digital B-mode reception data based on the RF data received from the transmitting and receiving unit 31, a computation unit 33 for making a predetermined computation on the RF data received from the transmitting and receiving unit 31, an image processing unit 34 for generating various items of image data, an input unit 35, realized by use of a user interface such as keyboard, mouse or touch panel, for receiving various items of input information, a control unit 36 for controlling the entire ultrasound diagnosis system 1, and a storage unit 37 for storing various items of information required for the operations of the ultrasound observation apparatus 3.

Figure 2:
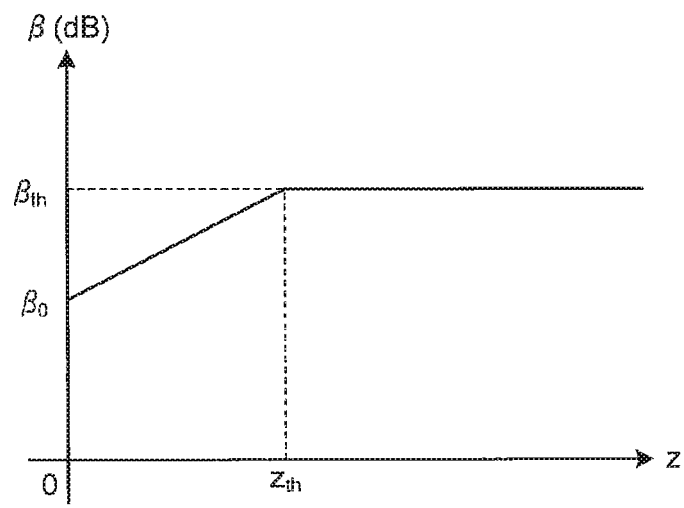
FIG. 2 is a diagram illustrating a relationship between reception depth and amplification rate in an amplification processing performed by a signal amplification unit in the ultrasound observation apparatus according to the first embodiment of the present invention.

The transmitting and receiving unit 31 has a signal amplification unit 311 for amplifying an echo signal. The signal amplification unit 311 makes a STC (Sensitivity Time Control) correction for amplifying an echo signal with a larger reception depth at a higher amplification rate. FIG. 2 is a diagram illustrating a relationship between reception depth and amplification rate in the amplification processing performed by the signal amplification unit 311. The reception depth z illustrated in FIG. 2 is calculated based on an elapsed time from the start of reception of an ultrasound wave. As illustrated in FIG. 2, the amplification rate $\beta$ (dB) linearly increases from $\beta_0$ to $\beta_{th}$ ($>\beta_0$) along with an increase in reception depth z when the reception depth z is smaller than a threshold $z_{th}$. The amplification rate $\beta$ (dB) takes a constant value $\beta_{th}$ when the reception depth z is the threshold $z_{th}$ or more. The value of the threshold $Z_{th}$ is such that an ultrasound signal received from an observation target is almost attenuated and noises are dominant. More generally, the amplification rate $\beta$ may monotonically increase along with an increase in reception depth z when the reception depth z is smaller than the threshold $z_{th}$. The relationship illustrated in FIG. 2 is previously stored in the storage unit 37.

The transmitting and receiving unit 31 performs a processing such as filtering on the echo signal amplified by the signal amplification unit 311, and then performs A/D conversion on the processed echo signal thereby to generate temporal-domain RF data and to output it to the signal processing unit 32 and the computation unit 33. When the ultrasound endoscope 2 has a structure for causing the ultrasound transducer 21 to electronically scan in which a plurality of devices are provided in an array shape, the transmitting and receiving unit 31 has a multichannel circuit for beam combination corresponding to the devices.

It is better that the frequency band of a pulse signal transmitted by the transmitting and receiving unit 31 is a wide band almost covering a linear response frequency band of electroacoustic conversion from a pulse signal into an ultrasound pulse in the ultrasound transducer 21. Further, it is better that various processing frequency bands of an echo signal in the signal amplification unit 311 are a wide band almost covering a linear response frequency band of acoustoelectric conversion from an ultrasound echo into an echo signal in the ultrasound transducer 21. Thereby, when a frequency spectrum approximation processing described below is performed, approximation can be made with high accuracy.

The transmitting and receiving unit 31 has a function of transmitting various control signals output by the control unit 36 to the ultrasound endoscope 2, and receiving various items of information including identification ID from the ultrasound endoscope 2 and transmitting them to the control unit 36.

The signal processing unit 32 performs a well-known processing such as bandpass filter, envelope curve detection or logarithmic conversion on the RF data thereby to generate digital B-mode reception data. The logarithmic conversion takes the common logarithm of the amount obtained by dividing the RF data by a reference voltage to be expressed in a decibel value. The signal processing unit 32 outputs the generated B-mode reception data to the image processing unit 34. The signal processing unit 32 is realized by use of the CPU (Central Processing Unit) or various computation circuits.

The computation unit 33 has an amplification correction unit 331 for making an amplification correction such that the amplification rate is constant for the RF data output by the transmitting and receiving unit 31 irrespective of the reception depth, a frequency analysis unit 332 for performing fast Fourier transform (FFT) on the amplification-corrected RF data thereby to make a frequency analysis and calculating a plurality of frequency spectra depending on the reception depth and the reception direction of an ultrasound signal, a frequency band setting unit 333 for setting a frequency band used for calculating a feature of each frequency spectrum calculated by the frequency analysis unit 332 by use of parameters associated with a frequency spectrum in each of a plurality of candidate bands having mutually different bandwidths, and a feature calculation unit 334 for calculating a feature of each frequency spectrum based on the frequency band set by the frequency band setting unit 333. The computation unit 33 is realized by use of the CPU or various computation circuits.

Figure 3:
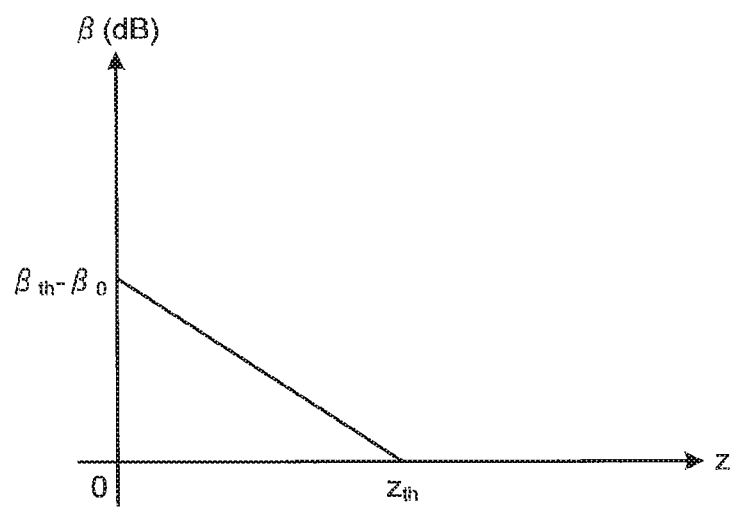
FIG. 3 is a diagram illustrating a relationship between reception depth and amplification rate in an amplification correction processing performed by an amplification correction unit in the ultrasound observation apparatus according to the first embodiment of the present invention.

FIG. 3 is a diagram illustrating a relationship between reception depth and amplification rate in the amplification correction processing performed by the amplification correction unit 331. As illustrated in FIG. 3, the amplification rate $\beta$ (dB) in the amplification processing performed by the amplification correction unit 331 takes a maximum value $\beta_{th}-\beta_0$ when the reception depth is zero, and linearly decreases until the reception depth z reaches the threshold $z_{th}$, and takes zero when the reception depth z is the threshold $z_{th}$ or more. The relationship illustrated in FIG. 3 is previously stored in the storage unit 37. The amplification correction unit 331 makes the amplification correction of the digital RF signal based on the relationship illustrated in FIG. 3, thereby compensating an effect of the STC correction in the signal amplification unit 311 and outputting a signal with a constant amplification rate $\beta_{th}$. It is natural that the relationship between the reception depth z and the amplification rate $\beta$ in the amplification correction unit 331 is different depending on a relationship between reception depth and amplification rate in the signal amplification unit 311.

The reasons for making the amplification correction will be described. The STC correction is a correction processing of amplifying amplitude of an analog signal waveform uniformly over the entire frequency bands and at an amplification rate monotonically increasing relative to a depth, thereby to eliminate an effect of attenuation from the amplitude of the analog signal waveform. Therefore, when a B-mode image displayed by converting amplitude of an echo signal into luminance is generated and when a tissue is uniformly scanned, the STC correction is made so that the luminance value is constant irrespective of depth. That is, it is possible to obtain die effect that an effect of attenuation is eliminated from the luminance value of the B-mode image.

On the other hand, when a frequency spectrum of an ultrasound wave is calculated and its analysis result is used as in the first embodiment, there is a problem that an effect of attenuation along with propagation of an ultrasound wave is not necessarily removed even by the STC correction. This is because the attenuation amount is generally different per frequency (see Equation (1) described below) but the amplification rate of the STC correction changes along with only a distance and is not frequency-dependent.

In order to solve the above problem, when a STC-corrected reception signal is output for generating a B-mode image, while an image based on a frequency spectrum is generated, new transmission different from transmission for generating the B-mode image is performed thereby to output a reception signal not subjected to the STC correction. In this case, there is a problem that a frame rate of the image data generated based on the reception signal is deteriorated.

Thus, according to the first embodiment, the frame rate of the generated image data is kept, while the amplification rate is corrected by the amplification correction unit 331 in order to eliminate an effect of the STC correction from the STC-corrected signal for B-mode image.

The frequency analysis unit 332 samples the RF data (line data) of each sound ray amplification-corrected by the amplification correction unit 331 at predetermined time intervals thereby to generate sample data. The frequency analysis unit 332 performs the FFT processing on sample data groups thereby to calculate the frequency spectra at a plurality of portions (data positions) on the RF data.

Figure 4:
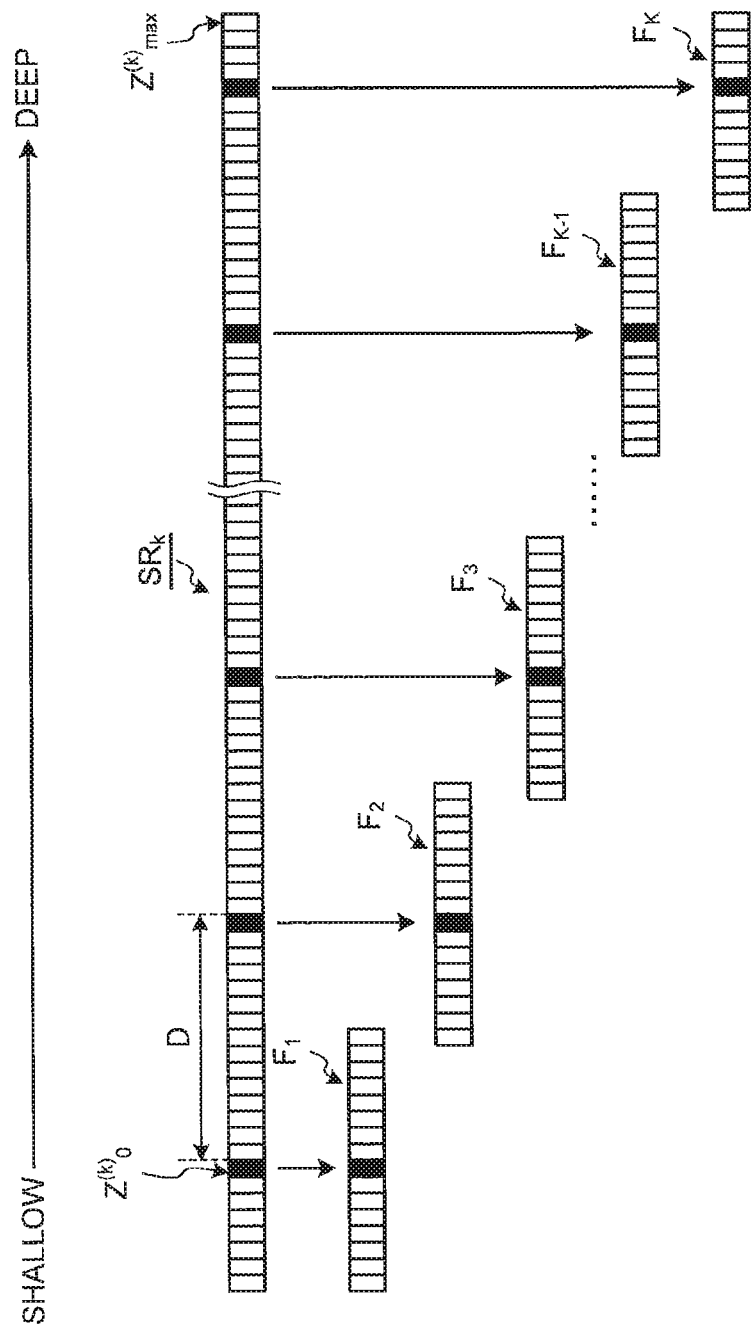
FIG. 4 is a diagram schematically illustrating a data arrangement in one sound ray of an ultrasound signal.

FIG. 4 is a diagram schematically illustrating a data arrangement in one sound ray of an ultrasound signal. In the illustrated sound ray $SR_k$, a white or black rectangle indicates data at a sample point. Further, in the sound ray $SR_k$, data toward the right side is sample data from a deeper portion when it is measured along the sound ray $SR_k$ from the ultrasound transducer 21 (see the arrows in FIG. 4). The sound ray $SR_k$ is discretized at time intervals corresponding to a sampling frequency (50 MHz, for example) in the A/D conversion performed by the transmitting and receiving unit 31. FIG. 4 illustrates that the eighth data position in the sound ray $SR_k$ with a number k is set as an initial value $Z^{(k)}_0$ in the direction of the reception depth z, but the position of the initial value can be arbitrarily set. A calculation result by the frequency analysis unit 332 is obtained in complex numbers, and is stored in the storage unit 37.

A group of data $F_j$ (j=1, 2, . . . , K) illustrated in FIG. 4 is a sample data group to be subjected to the FFT processing. Generally, the sample data group needs to have as much data as a power of 2 in order to perform the FFT processing. In this sense, the sample data group $F_j$ (j=1, 2, . . . , K−1) is a normal group of data including as much data as 16 (=$2^4$), while the sample data group $F_K$ is an abnormal group of data including as much data as 12. When the FFT processing is performed on the abnormal group of data, zero data is inserted to cover the shortfall thereby to generate a normal sample data group. This point will be described below in explaining the processing of the frequency analysis unit 332 (see FIG. 10).

A "frequency spectrum" calculated by the frequency analysis unit 332 indicates a "frequency distribution of intensities at a reception depth z" obtained by performing the FFT processing on a sample data group. "Intensity" herein indicates a parameter such as voltage of echo signal, power of echo signal, acoustic pressure of ultrasound echo or acoustic energy of ultrasound echo, amplitude or time integral value of the parameters, or a combination thereof.

Generally, a frequency spectrum indicates a different trend depending on a property of a biological tissue scanned by an ultrasound wave when an observation target is a biological tissue. This is because a frequency spectrum has a correlation with size of a scattering body for scattering ultrasound waves, number density, or acoustic impedance. A "property of a biological tissue" indicates malignant tumor (cancer), benign tumor, endocrine tumor, mucinous tumor, normal tissue, cyst, vascular channel, and the like, for example.

The frequency band setting unit 333 has an envelope curve detection unit 333a for detecting an envelope curve of a frequency spectrum, a parameter extraction unit 333b for extracting parameters associated with an approximation curve for approximating an envelope curve in a plurality of candidate bands including a frequency corresponding to a maximum value of the envelope curve detected by the envelope curve detection unit 333a per candidate band, a variation calculation unit 333c for calculating a variation between two parameters extracted in two candidate bands in a predetermined relationship among the parameters extracted per candidate band by the parameter extraction unit 333b, and a determination unit 333d for determining a frequency band based on the variation between the parameters calculated by the variation calculation unit 333c.

Figure 5:
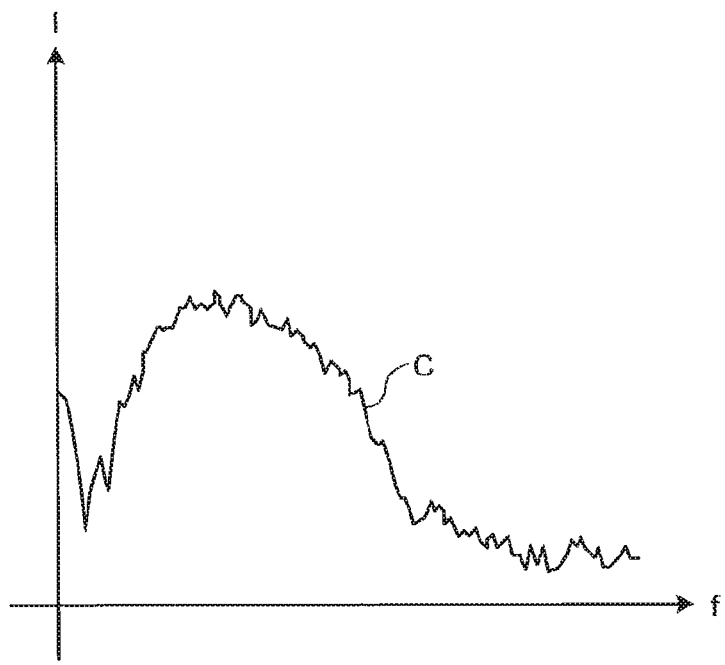
FIG. 5 is a diagram illustrating an exemplary envelope curve of a frequency spectrum detected by an envelope curve detection unit in the ultrasound observation apparatus according to the first embodiment of the present invention.

The envelope curve detection unit 333a detects an envelope curve of a frequency spectrum by use of a well-known envelope curve detection processing. FIG. 5 is a diagram illustrating an exemplary envelope curve of a frequency spectrum detected by the envelope curve detection unit 333a. The illustrated envelope curve C indicates a distribution of common logarithm (in dB) I=10 $\log_{10}$ ($I_0/I_c$) of the amount obtained by dividing an intensity $I_0$ by a reference intensity $I_c$ (constant) relative to a frequency f. According to the first embodiment, a curve and a line are made of a set of discrete points, respectively.

Figure 6:
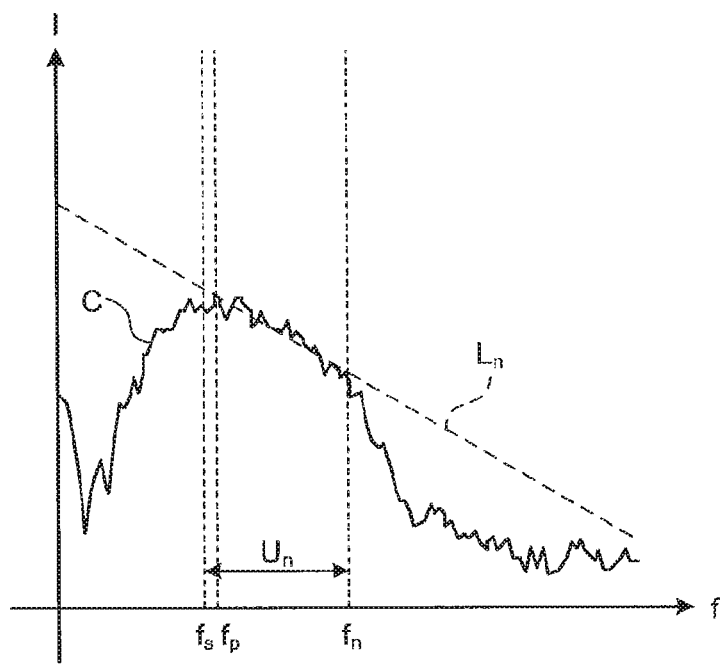
FIG. 6 is a diagram schematically illustrating an outline of a parameter extraction processing performed by a parameter extraction unit in the ultrasound observation apparatus according to the first embodiment of the present invention.

The parameter extraction unit 333b makes the regression analysis of the envelope curve detected by the envelope curve detection unit 333a in a candidate band thereby to linearly approximate the envelope curve, and extracts the slope of the approximated line as a parameter. FIG. 6 is a diagram schematically illustrating an outline of the parameter extraction processing performed by the parameter extraction unit 333b. The parameter extraction unit 333b calculates a line for approximating a candidate band $U_n$= (f1$f_s$<f<$f_n$) for the envelope curve C by the regression analysis, and determines the slope of the resultant approximate line (regression line) $L_n$ as a parameter. The start frequency $f_s$ in the candidate band $U_n$ is set as a frequency (constant) smaller than a peak frequency $f_p$ taking the maximum value of the envelope curve C by a predetermined value. The maximum frequency $f_n$ (n=0, 1, 2, . . . ) in the candidate band $U_n$ is at $f_n > f_{max}$, and $f_n = f_{n-1} + \Delta f$ ($\Delta f > 0$) is established. Herein, $\Delta f$ indicates a predetermined constant which is sufficiently lower than the start frequency $f_s$. The parameter extraction unit 333b calculates the slope of the line while increasing the value of n until the determination unit 333d determines a frequency band. The increase $\Delta f$ of the maximum frequency along with a change in the start frequency $f_s$ and the candidate band can be arbitrarily set, and may be set and input by the user via the input unit 35.

The variation calculation unit 333c calculates the value $P_{n+1} - P_n$ obtained by subtracting the parameter $P_n$ calculated in the candidate band $U_n$ from the parameter $P_{n+1}$ calculated in the candidate band $U_{n+1}$ as a variation $\Delta P_n$ between the parameters. The variation calculation unit 333c calculates the variation $\Delta P_n$ between parameters until the determination unit 333d determines a frequency band.

Figure 7:
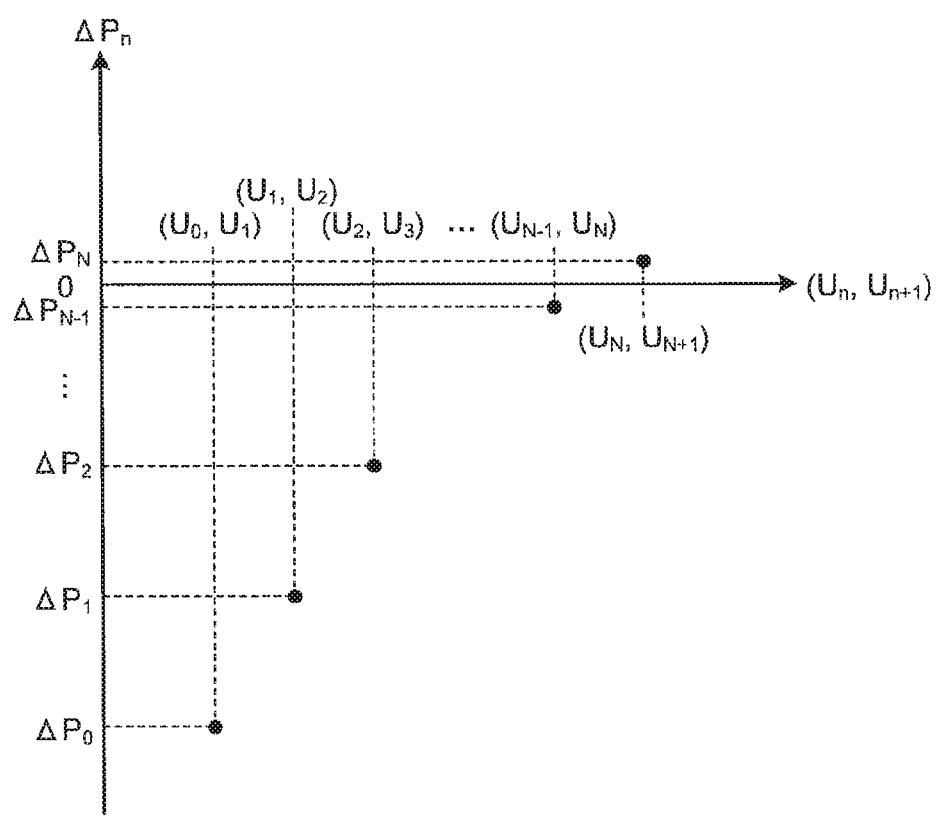
FIG. 7 is a diagram illustrating an outline of a frequency band determination processing performed by a determination unit in the ultrasound observation apparatus according to the first embodiment of the present invention.

The determination unit 333d determines a frequency band based on a sign of the variation between the parameters calculated by the variation calculation unit 333c. FIG. 7 is a diagram illustrating an outline of a frequency band determination processing performed by the determination unit 333d. In FIG. 7, the horizontal axis indicates two candidate bands ($U_n$, $U_{n+1}$) (n=0, 1, ...) for which a variation between parameters is calculated, and the vertical axis indicates a variation $\Delta P_n = P_{n+1} - P_n$ between parameters in the two candidate bands ($U_n$, $U_{n+1}$). In the case of FIG. 7, $\Delta P_n \leq 0$ is satisfied when the value of n indicating the two candidate bands ($U_n$, $U_{n+1}$) is n=0, 1, ..., N-1, while $\Delta P_n$ ($= \Delta P_N$) > 0 is satisfied when the value of n is n=N. The determination unit 333d sets the candidate band $U_N$ with a smaller band out of the two candidate bands ($U_N$, $U_{N+1}$) as a frequency band when the variation $\Delta P_n$ between the parameters changes from "0 or less" to "positive." The maximum frequency $f_N$ of the candidate band $U_N$ as frequency band is denoted as end frequency $f_e$.

The feature calculation unit 334 has an approximation unit 334a for approximating an envelope curve with a frequency spectrum by a line by the regression analysis thereby to calculate a pre-correction feature of the frequency spectrum, and an attenuation correction unit 334b for making an attenuation correction based on each of a plurality of attenuation candidate values on the pre-correction feature calculated by the approximation unit 334a thereby to calculate a corrected feature.

Figure 8:
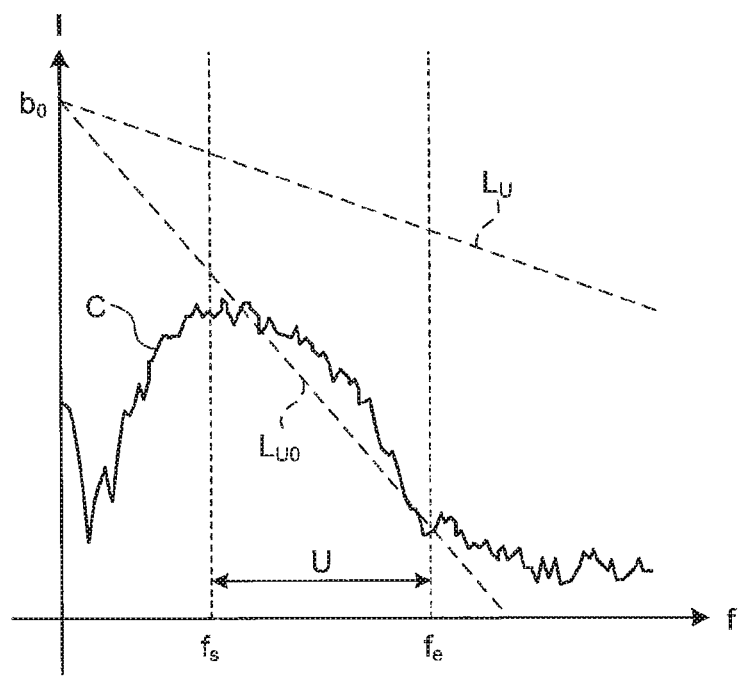
FIG. 8 is a diagram illustrating an outline of an approximation processing performed by an approximation unit in the ultrasound observation apparatus according to the first embodiment of the present invention.

The approximation unit 334a makes the regression analysis of an envelope curve with a frequency spectrum in a predetermined frequency band and approximates it in a linear equation, thereby calculating a pre-correction feature characterizing the linear equation to approximate. For example, in the case of the envelope curve C illustrated in FIG. 5, the approximation unit 334a makes the regression analysis in the frequency band (candidate band) set by the frequency band setting unit 333 thereby to obtain an approximate line of the envelope curve C. FIG. 8 is a diagram illustrating an outline of an approximation processing performed by the approximation unit 334a. The line $L_{U0}$ illustrated in FIG. 8 is an approximate line obtained by approximating the envelope curve C in the candidate band U by the linear equation $I = a_0 f + b_0$. The approximation unit 334a calculates slope $a_0$, intercept $b_0$, and mid-band fit $c_0 = a_0 f_M + b_0$ as the value of the intensity I at the center frequency $f_M = (f_s + f_e)/2$ in the candidate band U, as the pre-correction features corresponding to the line $L_{U0}$. The approximation unit 334a may approximate a frequency spectrum by a second-order or higher polynomial equation using regression analysis.

Among the three pre-correction features, the slope $a_0$ has a correlation with a size of the scattering body of an ultrasound wave, and it is generally believed that as the scattering body is larger, the slope has a smaller value. The intercept $b_0$ has a correlation with a size of the scattering body, a difference in acoustic impedance, a number density (density) of the scattering body, and the like. Specifically, it is believed that the intercept $b_0$ has a larger value as the scattering body is larger, has larger value as the difference in acoustic impedance is larger, and has a larger value as the number density of the scattering body is larger. The mid-band fit $c_0$ is an indirect parameter derived from the slope $a_0$ and the intercept $b_0$, and gives an intensity of a spectrum at the center of an effective frequency band. Therefore, the mid-band fit $c_0$ is assumed to have a certain correlation with luminance of a B-mode image in addition to the size of the scattering body, the difference in acoustic impedance, and the number density of the scattering body.

The attenuation correction unit 334b makes an attenuation correction by use of an attenuation rate giving attenuation of an ultrasound wave per unit length and unit frequency. Generally, attenuation A(f, z) of an ultrasound wave is defined as attenuation occurring while an ultrasound wave reciprocates between the reception depth 0 and the reception depth z and a change in intensity between after and before the reciprocation (difference in dB). It is empirically known that the attenuation A(f, z) is proportional to a frequency in a uniform tissue, which is expressed in the following Equation (1).

$$A(f, z) = 2\alpha z f \quad (1)$$

where the proportional constant $\alpha$ indicates the amount called attenuation, and gives attenuation of an ultrasound wave per unit length and unit frequency. z indicates a reception depth of an ultrasound wave, and f indicates a frequency. A specific value of the attenuation $\alpha$ is defined depending on a site of a biological body when an observation target is a biological body. The unit of the attenuation $\alpha$ is dB/cm/MHz, for example.

The attenuation correction unit 334b makes the attenuation correction of the pre-correction features (slope $a_0$, intercept $b_0$, and mid-band fit $c_0$) extracted by the approximation unit 334a according to the following Equations (2) to (4) thereby to calculate the corrected features a, b, and c.

$$a = a_0 + 2\alpha z \quad (2)$$

$$b = b_0 \quad (3)$$

$$c = c_0 + A(f_M, Z) = c_0 2\alpha z f_M (= a f_M + b) \quad (4)$$

As is clear from the Equations (2) and (4), the attenuation correction unit 334b makes the correction with a larger correction amount as the reception depth z of an ultrasound wave is larger. From the Equation (3), the correction for the intercept is identical transformation. This is because the intercept is a frequency component corresponding to the frequency 0 (Hz) and is not influenced by attenuation.

The line $L_U$ illustrated in FIG. 8 is a line having the correction features a, b, and c corrected by the attenuation correction unit 334b as parameters. The equation for the line $L_U$ is expressed as:

$$I = af + b = (a_0 + 2\alpha z)f + b_0 \quad (5)$$

As is clear from the Equation (5), the line $L_U$ has a larger slope than the line $L_{U0}$ not subjected to the attenuation correction ($a > a_0$), and has the same intercept ($b = b_0$).

The image processing unit 34 has a B-mode image data generation unit 341 for generating B-mode image data which is an ultrasound image displaying the amplitude of an echo signal converted into luminance, and a feature image data generation unit 342 for generating feature image data displaying information on the features calculated by the feature calculation unit 334.

The B-mode image data generation unit 341 generates B-mode image data by performing a signal processing using well-known technique such as a gain processing or a contrast processing on B-mode reception data received from the signal processing unit 32, and thinning data depending on a data step width defined depending on an image display range in the display device 4. The B-mode image is a gray scale image in which the values of the variables R (red), G (green), and B (Blue) are matched with each other when the color space employs a RGB color system.

The B-mode image data generation unit 341 performs coordinate conversion on the B-mode reception data such that the scanning range can be spatially correctly expressed, and then embeds a gap between the B-mode reception data by performing an interpolation processing between the B-mode reception data, thereby generating B-mode image data. The B-mode image data generation unit 341 outputs the generated B-mode image data to the feature image data generation unit 342.

The feature image data generation unit 342 superimposes visual information associated with the features calculated by the feature calculation unit 334 on each pixel in an image in the B-mode image data thereby to generate feature image data. The feature image data generation unit 342 assigns the visual information corresponding to the features of the frequency spectrum calculated from a group of amplitude data $F_j$ to the pixel regions corresponding to the amount of data of a sample data group $F_j$ (j=1, 2, . . . , K) illustrated in FIG. 4, for example. The feature image data generation unit 342 associates hue as visual information with any one of slope, intercept, and mid-band fit described above thereby to generate feature image data. The feature image data generation unit 342 associates hue to either of the two features selected from among slope, intercept and mid-band fit, and associates contrast to the other thereby to generate feature image data. The visual information associated with the features may include the variables of a color space configuring a predetermined color system such as color saturation, luminance value, R (red), G (green), and B (Blue) in addition to hue and contrast (brightness).

The control unit 36 is realized by use of the CPU (Central Processing Unit) having the computation and control functions, or various computation circuits. The control unit 36 reads information stored in the storage unit 37 from the storage unit 37 and performs various computation processing associated with the method for operating the ultrasound observation apparatus 3 thereby to organize and control the ultrasound observation apparatus 3. The control unit 36 may be configured by use of the common CPU with the signal processing unit 32 and the computation unit 33.

The storage unit 37 has a spectrum information storage unit 371 for storing the information on the frequency spectrum calculated by the frequency analysis unit 332 together with the reception depth and the reception direction, a parameter information storage unit 372 for storing the information on the parameters extracted per candidate band by the parameter extraction unit 333b, and a frequency band information storage unit 373 for storing the information on the frequency band set by the frequency band setting unit 333.

The storage unit 37 stores the information such as the information required for the amplification processing (the relationship between amplification rate and reception depth illustrated in FIG. 2), the information required for the amplification correction processing (the relationship between amplification rate and reception depth illustrated in FIG. 3), the information required for the attenuation correction processing (see Equation (1)), and the window functions (such as Hamming, Hanning, and Blackman) required for the frequency analysis processing in addition to the above.

The storage unit 37 stores various programs including an operation program for performing the method for operating the ultrasound observation apparatus 3. The operation program can be recoded in a computer readable recording medium such as hard disk, flash memory, CD-ROM, DVD-ROM, or flexible disk to be widely distributed. The various programs can be downloaded and obtained via a communication network. The communication network described herein is realized by existing public line network, LAN (Local Area Network), WAN (wide Area Network), or the like, and may be wired or wireless.

The storage unit 37 having the above structure is realized by use of ROM (Read Only Memory) previously installing various programs therein, RAN (Random Access Memory) storing computation parameters or data of each processing therein, or the like.

Figure 9:
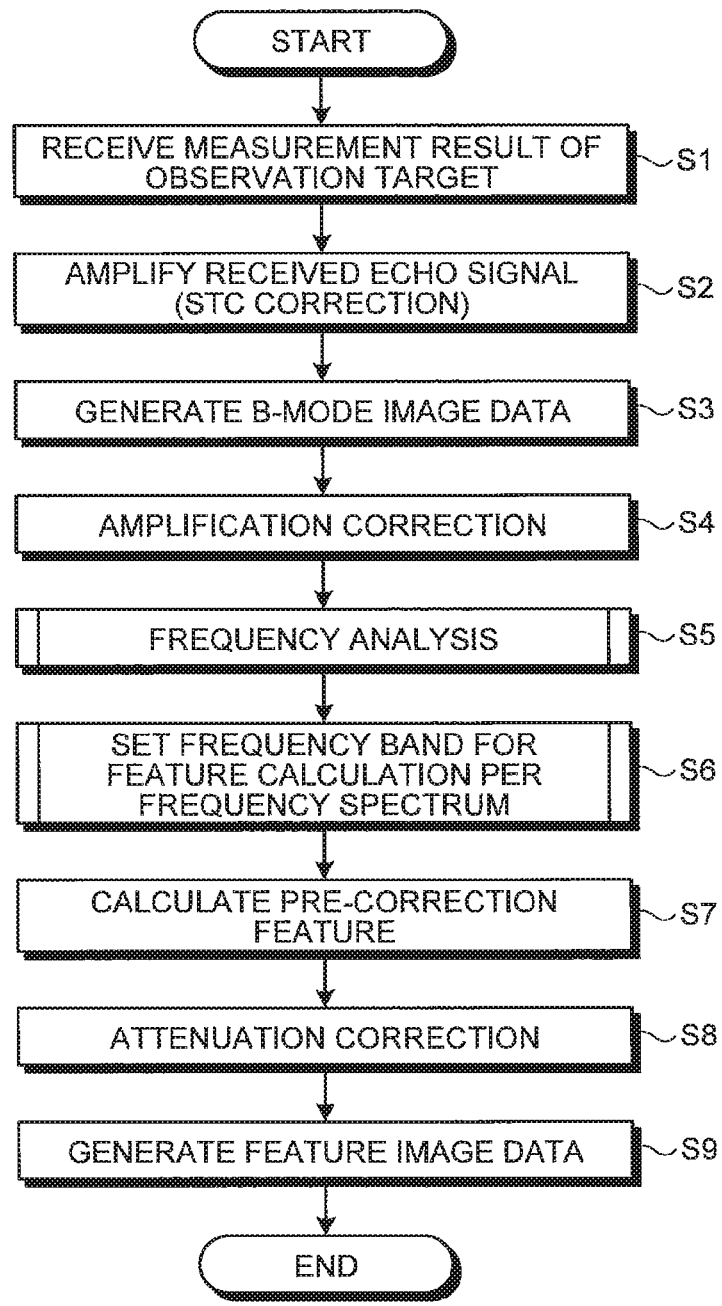
FIG. 9 is a flowchart illustrating an outline of the processing performed by the ultrasound observation apparatus according to the first embodiment of the present invention.

FIG. 9 is a flowchart illustrating an outline of the processing performed by the ultrasound observation apparatus 3 having the above structure. Specifically, it is a flowchart illustrating an outline of the processing after the ultrasound observation apparatus 3 receives an echo signal from the ultrasound endoscope 2. The processing performed by the ultrasound observation apparatus 3 will be described below with reference to FIG. 9. At first, the ultrasound observation apparatus 3 receives an echo signal as a measurement result of an observation target by the ultrasound transducer 21 from the ultrasound endoscope 2 (step S1).

The signal amplification unit 311 which receives the echo signal from the ultrasound transducer 21 amplifies the echo signal (step S2). Herein, the signal amplification unit 311 amplifies (makes the STC correction of) the echo signal based on the relationship between amplification rate and reception depth illustrated in FIG. 2, for example.

Subsequently, the B-mode image data generation unit 341 generates B-mode image data by use of the echo signal amplified by the signal amplification unit 311 and outputs it to the display device 4 (step S3). The display device 4 which receives the B-mode image data displays a B-mode image corresponding to the B-mode image data.

The amplification correction unit 331 makes the amplification correction of the RF data output from the transmitting and receiving unit 31 such that the amplification rate is constant irrespective of the reception depth (step S4). Herein, the amplification correction unit 331 makes the amplification correction based on the relationship between amplification rate and reception depth illustrated in FIG. 3, for example.

Figure 10:
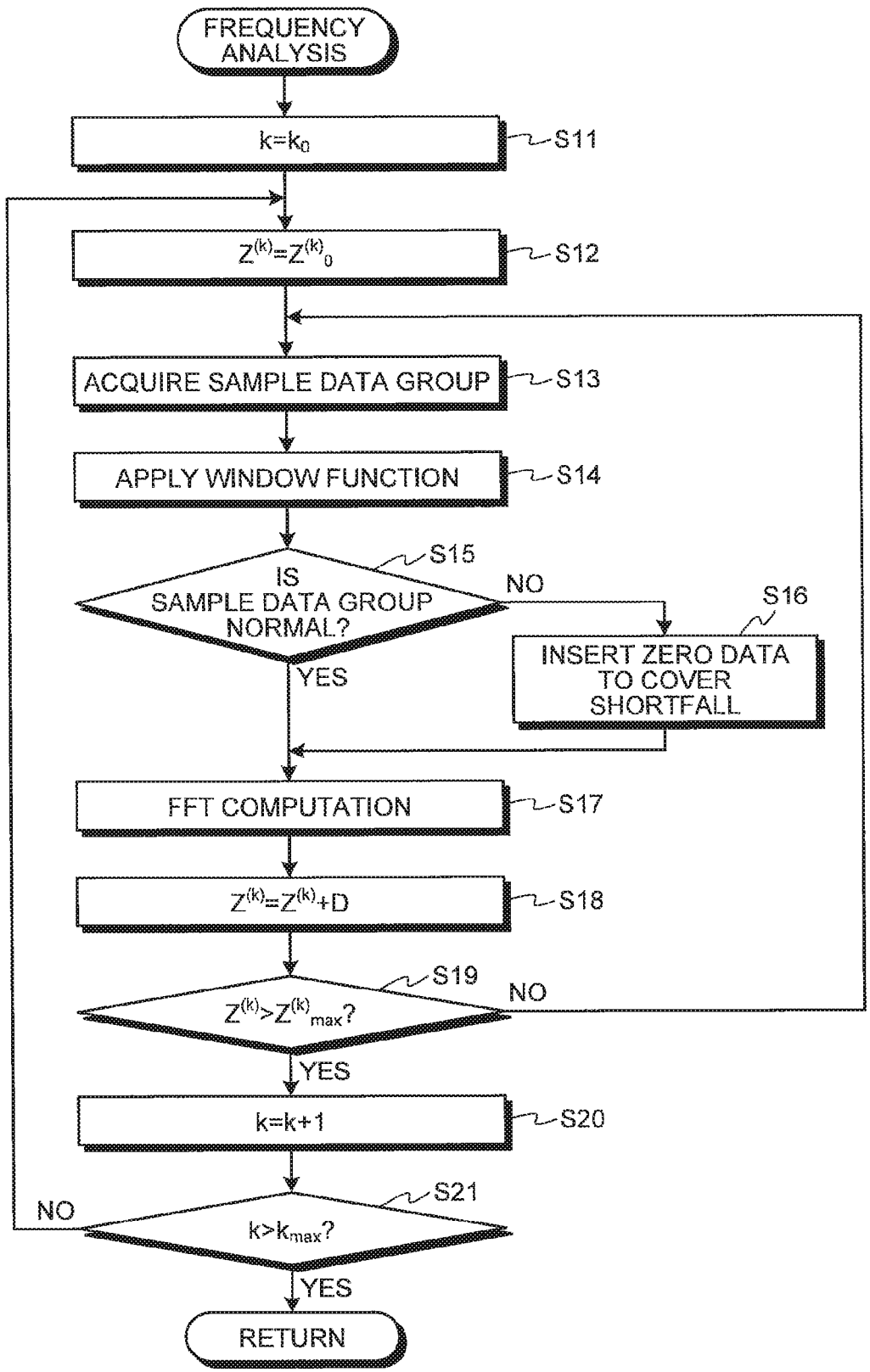
FIG. 10 is a flowchart illustrating an outline of a processing performed by a frequency analysis unit in the ultrasound observation apparatus according to the first embodiment of the present invention.

Thereafter, the frequency analysis unit 332 makes the FFT frequency analysis of the RF data of each amplification-corrected sound ray thereby to calculate the frequency spectra for all the sample data groups to be stored in the spectrum information storage unit 371 (step S5). FIG. 10 is a flowchart illustrating an outline of the processing performed by the frequency analysis unit 332 in step S5. The frequency analysis processing will be described below in detail with reference to the flowchart illustrated in FIG. 10.

At first, the frequency analysis unit 332 sets a counter k for identifying an sound ray to be analyzed as $k_0$ (step S11).

Subsequently, the frequency analysis unit 332 sets an initial value $Z^{(k)}_0$ at a data position (corresponding to the reception depth) $Z^{(k)}$ representative of a series of groups of data (sample data groups) generated for the FFT computation (step S12). For example, FIG. 4 illustrates that the eighth data position in the sound ray $SR_k$ is set as the initial value $Z^{(k)}_0$ as described above.

Thereafter, the frequency analysis unit 332 acquires a sample data group (step S13) and applies the window function stored in the storage unit 37 to the acquired sample data group (step 14). The window function is applied to the sample data group in this way thereby to avoid the sample data group from being discontinuous at their boundaries and preventing artifact from occurring.

Subsequently, the frequency analysis unit 332 determines whether the sample data group at the data position $Z^{(k)}$ a normal group of data (step S15). As described with reference to FIG. 4, the sample data group needs to have as much data as a power of 2. In the following, the number of items of data in a normal sample data group is $2^n$ (n is a positive integer). According to the embodiment, the data position $Z^{(k)}$ is set at the center of a sample data group to which $Z^{(k)}$ belongs as far as possible. Specifically, the number of items of data in a sample data group is $2^n$, and thus $Z^{(k)}$ is set at the $2^n/2$ ($=2^{n-1}$)-th position near the center of the sample data group. In this case, a normal sample data group indicates that $2^{n-1}-1$ ($=N$) items of data are present at a shallower side than the data position. $Z^{(k)}$ and $2^{n-1}$ ($=M$) items of data are present at a deeper side than the data position $Z^{(k)}$. In the case illustrated in FIG. 4, the sample data group $F_j$ (j=1, 2, . . . , K−1) is normal. FIG. 4 illustrates the case with n=4 (N=7, M=8).

As a result of the determination in step S15, when the sample data group at the data position $Z^{(k)}$ is normal (step S15: Yes), the frequency analysis unit 332 proceeds to step S17 described below As a result of the determination in step S15, when the sample data group at the data position $Z^{(k)}$ is not normal (step S15: No), the frequency analysis unit 332 inserts zero data to cover the shortfall thereby to generate a normal sample data group (step S16). The window function is operated on the sample data group (the sample data group $F_K$ in FIG. 4, for example) determined as not normal in step S15 before zero data is added. Therefore, even when zero data is inserted into the group of sampled data, discontinuity between the data is not caused. After step S16, the frequency analysis unit 332 proceeds to step S17 described below.

In step S17, the frequency analysis unit 332 performs the FFT computation by use of the sample data group thereby to obtain a frequency spectrum as a frequency distribution of amplitudes (step S17).

Subsequently, the frequency analysis unit 332 changes the data position $Z^{(k)}$ the step width D (step S18). The step width D is stored in the storage unit 37 in advance. FIG. 4 illustrates the case with D=15. The step width D is desirably matched with the data step width used when the B-mode image data generation unit 341 generates B-mode image data, but when the computation amount by the frequency analysis unit 332 is to be reduced, the step width D may be set to be larger than the data step width.

Thereafter, the frequency analysis unit 332 determines whether the data position $Z^{(k)}$ larger than a maximum value $Z^{(k)}_{max}$ in the sound ray $SR_k$ (step S19). When the data position $Z^{(k)}$ is larger than the maximum value $Z^{(k)}_{max}$ (step S19: Yes), the frequency analysis unit 332 increments the counter k by 1 (step S20). This indicates that the processing proceeds to a next sound ray. On the other hand, when the data position $Z^{(k)}$ is the maximum value $Z^{(k)}_{max}$ or less (step S19: No), the frequency analysis unit 332 returns to step S13.

After step S20, the frequency analysis unit 332 determines whether the counter k is larger than a maximum value $k_{max}$ (step S21). When the counter k is larger than the maximum value $k_{max}$ (step S21: Yes), the frequency analysis unit 332 terminates the series of frequency analysis processing. On the other hand, when the counter k is the maximum value $k_{max}$ or less (step S21: No), the frequency analysis unit 332 returns to step S12. The maximum value $k_{max}$ is a value arbitrarily designated and input by the user such as operator via the input unit 35, or a value previously set in the storage unit 37.

In this way, the frequency analysis unit 332 performs the FFT computation several times on each of ($k_{max}-k_0+1$) sound rays within a region to be analyzed. A frequency spectrum obtained as a result of the FFT computation is stored in the spectrum information storage unit 371 together with the reception depth, the reception direction and identification information. The identification information herein is directed for identifying a frequency spectrum during a frequency band setting processing described below, and includes an identification number i=0, 1, 2, . . . , $i_{max}$ sequentially given to each frequency spectrum, for example. According to the first embodiment, the identification number i has a counter function in the frequency band setting processing described below.

In the above explanation, the frequency analysis unit 332 performs the frequency analysis processing on all the regions in which an ultrasound signal is received, but the input unit 35 may accept an input of setting a partial region segmented by a specific depth width and sound ray width thereby to perform the frequency analysis processing only in the set partial region.

Figure 11:
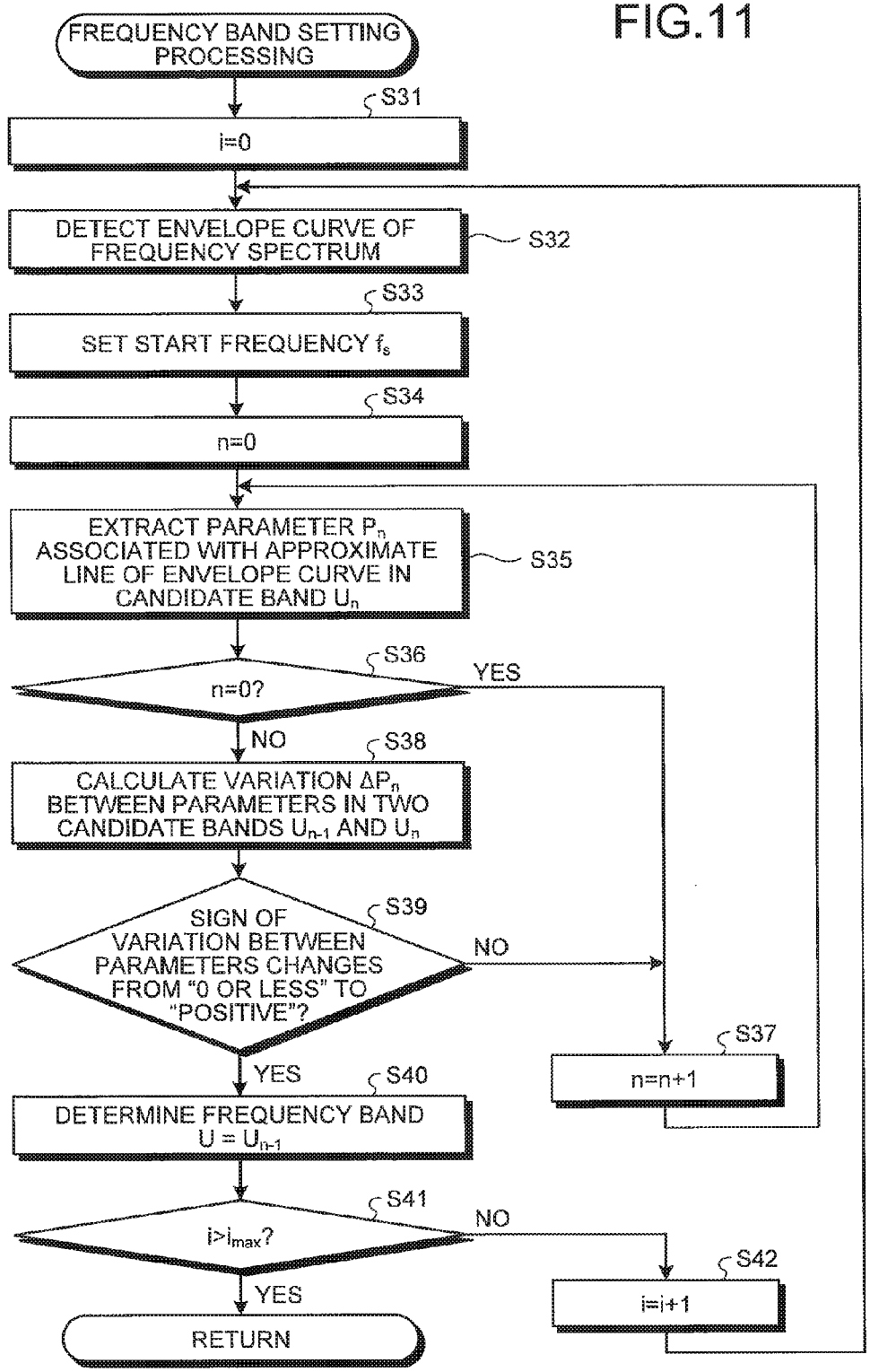
FIG. 11 is a flowchart illustrating an outline of a frequency band setting processing performed by a frequency band setting unit in the ultrasound observation apparatus according to the first embodiment of the present invention.

Subsequent to the frequency analysis processing in step S5 described above, the frequency band setting unit 333 sets a frequency band for feature calculation per frequency spectrum (step S6). FIG. 11 is a flowchart illustrating an outline of the frequency band setting processing in step S6. The frequency band setting processing will be described below in detail with reference to FIG. 11.

At first, the frequency band setting unit 333 sets a counter i for identifying a frequency spectrum at 0 (step S31).

Subsequently, the envelope curve detection unit 333a obtains a frequency spectrum corresponding to the counter i from the spectrum information storage unit 371, and detects an envelope curve of the obtained frequency spectrum (step S32). Consequently, the envelope curve C illustrated in FIG. 5 is detected, for example.

Thereafter, the parameter extraction unit 333b sets the start frequency $f_s$ (step S33). Specifically, the parameter extraction unit 333b extracts the peak frequency $f_p$ corresponding to the peak value of the intensity of the envelope curve to be processed, and determines a frequency smaller than the peak frequency $f_p$ by a predetermined value as the start frequency $f_s$. Step S33 may be a processing of reading and setting the value of the start frequency $f_s$ previously set and input by the user via the input unit 35 from the storage unit 37.

The parameter extraction unit 333b sets a repetitive counter n at 0 (step S34). Subsequently, the parameter extraction unit 333b calculates an approximate line of the envelope curve in the candidate band $U_n=\{f|f_s<f<f_n\}$ by the regression analysis and extracts the slope of the approximate line as parameter $P_n$ to be written and stored in the parameter information storage unit 372 (step S35).

Thereafter, the parameter extraction unit 333b determines whether the counter n is 0 (step S36). When the counter n is 0 (step S36: Yes), the parameter extraction unit 333b increments the counter n by 1 (step S37), and returns to the processing in step S35. Herein, when the counter n is incremented by 1, the value of the maximum frequency in the candidate band increments by Δf as described above. When the counter n is not 0 (step S36: No), the parameter extraction unit 333b proceeds to the processing in step S38.

In step S38, the variation calculation unit 333c calculates a difference in slope of the approximate lines in two candidate bands ($U_{n-1}$, $U_n$) as the parameter variation (step S38). Specifically, the variation calculation unit 333c subtracts the slope (parameter $P_{n-1}$) of the approximate line in the candidate band U from the slope (parameter $P_n$) of the approximate line in the candidate band $U_n$ calculated by the parameter extraction unit 333b thereby to calculate the parameter variation $\Delta P_n = P_{n+1} - P_n$, and writes and stores the calculation result into the parameter information storage unit 372.

The determination unit 333d determines whether the sign of the parameter variation calculated by the variation calculation unit 333c changes from "0 or less" to "positive" (step S39). Specifically, when the sign of the latest variation amount $\Delta P_n$ calculated by the variation calculation unit 333c is "positive," the determination unit 333d confirms whether the sign of the parameter variation $\Delta P_{n-1}$ previously calculated by the variation calculation unit 333c is "0 or less," thereby determining whether the sign of the parameter variation changes from "0 or less" to "positive." As a result of the determination, when the sign of the parameter variation changes from "0 or less" to "positive" (step S39: Yes), the determination unit 333d determines the candidate band $U_{n-1}$ as the frequency band U (step S40). For example, FIG. 7 illustrates that the candidate band $U_N$ (N=n−1) is set as the frequency band U. On the other hand, as a result of the determination, when the sign of the parameter variation does not change from "0 or less" to "positive" (step S39: No), the frequency band setting unit 333 proceeds to the processing in step S37.

Thereafter, the frequency band setting unit 333 determines whether the counter i is larger than a predetermined value $i_{max}$ (step S41). As a result of the determination, when $i > i_{max}$ is established (step S41: Yes), the frequency band setting unit 333 terminates the frequency band setting processing. On the other hand, as a result of the determination, when $i \leq i_{max}$ is established (step S41: No), the frequency band setting unit 333 increments the counter i by 1 (step S42), and returns to the processing in step S32.

After the frequency band setting processing in step S6 described above, the approximation unit 334a calculates the pre-correction features based on the approximate line in the frequency band U={f|$f_s \leq f \leq f_c$} (step S7). The pre-correction feature may be at least one of slope, intercept, mid-band fit of an approximate line described above, for example.

Subsequently, the attenuation correction unit 334b makes the attenuation correction of the pre-correction features (step S8). Thereby, the feature, in which an influence of attenuation in ultrasound propagation is eliminated, is calculated. In the case illustrated in FIG. 8, the line $L_U$ is obtained as a result of the attenuation correction processing.

Thereafter, the feature image data generation unit 342 generates feature image data by use of the features calculated in step S8 and the B-mode image data generated in step S3 (step S9). The feature image data generation unit 342 transmits the generated feature image data to the display device 4. The display device 4 which receives the feature image data displays a feature image corresponding to the received feature image data.

After step S9, the ultrasound observation apparatus 3 terminates the series of processing. The ultrasound observation apparatus 3 periodically and repeatedly performs the processing in steps S1 to S9.

Figure 12:
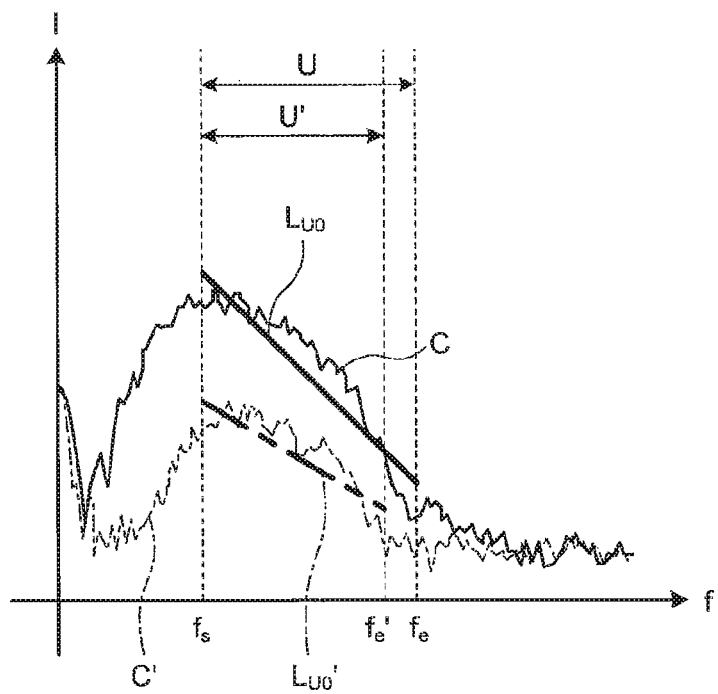
FIG. 12 is a diagram for explaining the effects of the first embodiment of the present invention.

FIG. 12 is a diagram for explaining the effects of the first embodiment. In FIG. 12, the envelope curve C' is detected from a frequency spectrum of the tissue having different tissue characteristics at the same reception depth as the envelope curve C. Specifically, it is illustrated that the particle diameter of the tissue in the envelope curve C is larger than the particle diameter of the tissue in the envelope curve C'. The line $L_{U0}$' is an approximate line calculated by the approximation unit 334a for the frequency band U'={f|$f_s' \leq f \leq f_e'$} set for the envelope curve C'. According to the first embodiment, a frequency band for feature calculation is adaptively determined, and thus the frequency band U set in the envelope curve C is different from the frequency band U' set in the envelope curve C'. Consequently, the slopes of the approximate lines $L_{U0}$ and $L_{U0}$' in the frequency bands U and U' are obviously different.

Figure 13:
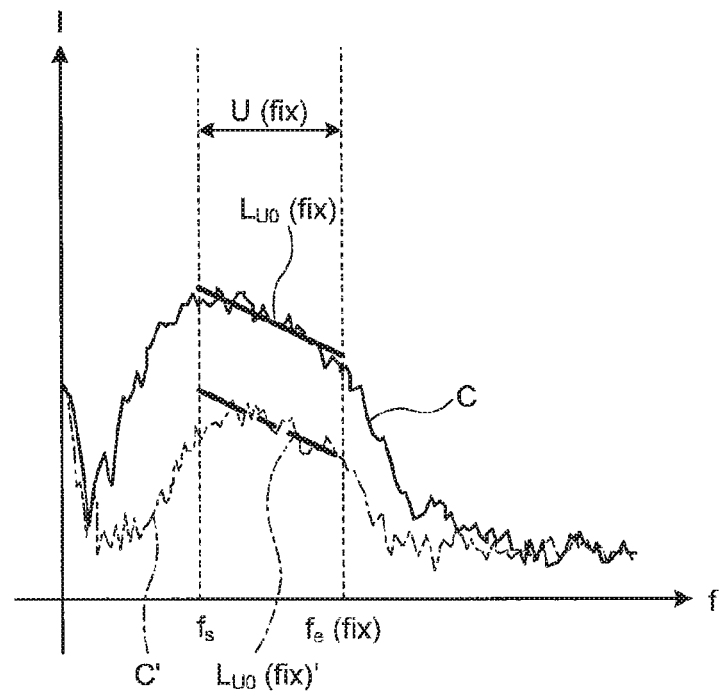
FIG. 13 is a diagram for explaining an outline of a conventional technique.

To the contrary, a conventional technique employs the same frequency band at the same reception depth. FIG. 13 is a diagram illustrating the approximate lines obtained when the conventional technique is applied to the same envelope curves C and C' as in FIG. 12 for comparison. In the case illustrated in FIG. 13, the approximate lines are found in the same frequency band U(fix)={f|$f_s \leq f \leq f_e$(fix)} for the envelope curves C and C'. Consequently, a large difference is not caused between the slope of the approximate line $L_{U0}$ (fix) for the envelope curve C and the slope of the approximate line $L_{U0}$ (fix)' for the envelope curve C', and thus the two tissues cannot be obviously distinguished.

In this way, according to the first embodiment of the present invention, an optimum frequency band for analysis is adaptively determined when a frequency spectrum is approximated, and thus different tissue characteristics even at the same reception depth can be more obviously distinguished as compared with the conventional technique in which a frequency band is fixed at least per reception depth. Therefore, according to the first embodiment, it is possible to distinguish tissue characteristics of the observation target with a high degree of accuracy.

Further, according to the first embodiment, the slopes of the approximate lines are extracted as the parameters associated with an approximate line for approximating an envelope curve in a plurality of candidate bands, and a variation between two parameters extracted in two candidate band, for which the values of the bandwidths of the candidate bands are adjacent among the parameters extracted per candidate band, is calculated, and a frequency band is determined based on a change in the sign of the variation, thereby finely setting a frequency band depending on tissue characteristics.

According the first embodiment, the parameter extraction unit 333b may linearly approximate an envelope curve by making the regression analysis of the envelope curve detected by the envelope curve detection unit 333a in a candidate band thereby to extract the intercept of the approximate line as a parameter.

First Modification of First Embodiment

Figure 14:
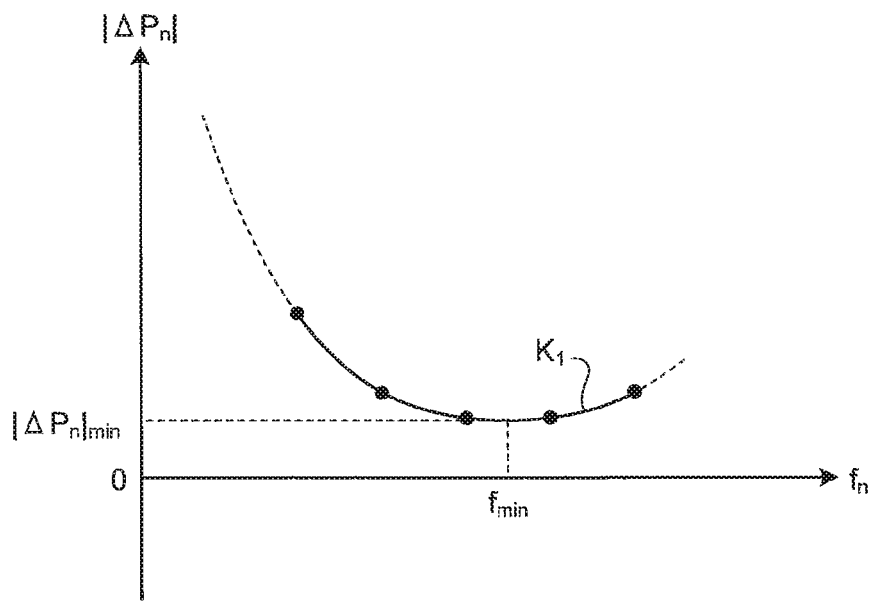
FIG. 14 is a diagram illustrating an outline of a frequency band setting processing performed by the frequency band setting unit in the ultrasound observation apparatus according to a first modification of the first embodiment of the present invention.

FIG. 14 is a diagram illustrating an outline of a frequency band setting processing according to a first modification of the first embodiment. In the first modification, the parameter extraction unit 333b extracts the parameters $P_n$ for a plurality of candidate bands $U_n$ (n=1, 2, ..., $n_{max}$). Subsequently, the variation calculation unit 333c calculates a parameter variation $\Delta P_n$ in two candidate regions ($U_n$, $U_{n+1}$) for the candidate bands $U_n$ as in the first embodiment. The determination unit 333d calculates an approximate curve in which an absolute value $|\Delta P_n|$ of the parameter variation $\Delta P_n$ is represented as a function of the maximum frequency $f_n$ in the candidate band $U_n$ with a smaller bandwidth out of the two candidate bands. The approximate curve is obtained by the regression analysis, for example. The curve $K_1$ illustrated in FIG. 14 is an exemplary approximate curve according to the first modification. The determination unit 333d determines a frequency band by assuming the frequency $f_{min}$ at the minimum value $|\Delta P_n|_{min}$ of the absolute value $|\Delta P_n|$ as the end frequency $f_e$ in the curve $K_1$.

According to the first modification, the similar effects as in the first embodiment can be obtained. Further, according to the first modification, the frequency bands can be set more finely, thereby further enhancing an accuracy of distinguishing tissue characteristics.

Second Modification of First Embodiment

Figure 15:
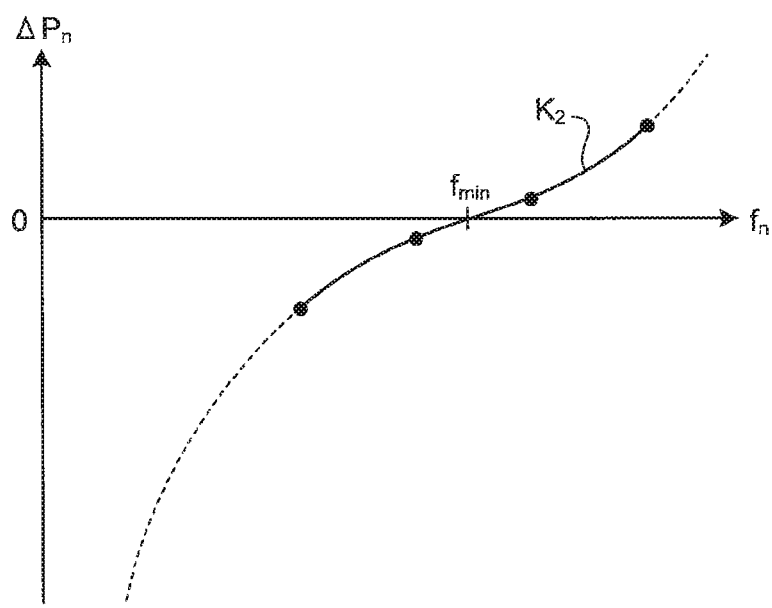
FIG. 15 is a diagram illustrating an outline of a frequency band setting processing performed by the frequency band setting unit in the ultrasound observation apparatus according to a second modification of the first embodiment of the present invention.

FIG. 15 is a diagram illustrating an outline of a frequency band setting processing according to a second modification of the first embodiment. According to the second modification, the parameter extraction unit 333b extracts the parameters $P_n$ for a plurality of candidate bands $U_n$ (n=1, 2, ..., $n_{max}$). Subsequently, the variation calculation unit 333c calculates a parameter variation $\Delta P_n$ in two candidate regions ($U_n$, $U_{n+1}$) as in the first embodiment. Thereafter, the determination unit 333d calculates an approximate curve with the parameter variation $\Delta P_n$ as a function of the maximum frequency $f_n$ of the candidate region $U_n$ for which the bandwidth is smaller out of the two candidate bands. The approximate curve is also obtained by the regression analysis, for example. The curve $K_2$ illustrated in FIG. 15 is an exemplary approximate curve according to the second modification. The determination unit 333d sets a frequency band with the frequency $f_{min}$ with $\Delta P_n=0$ as the end frequency $f_e$ in the curve $K_2$.

According to the second modification, the similar effects as in the first embodiment can be obtained. Further, according to the second modification, the frequency bands can be set more finely as in the first modification, thereby further enhancing an accuracy of distinguishing tissue characteristics.

Second Embodiment

A second embodiment of the present invention is different from the first embodiment in the parameter calculation method performed by the parameter extraction unit 333b. Specifically, according to the second embodiment, the parameter extraction unit 333b calculates a frequency distribution when sampling points are projected onto a plurality of projection lines set in plane with an envelope curve, determines a projection line with the smallest statistical variation in the found frequency distribution, and extracts the slope of a line orthogonal to the projection line as a parameter of the envelope curve. The structure of the ultrasound observation apparatus according to the second embodiment is the same as the structure of the ultrasound observation apparatus 3 described according to the first embodiment.

Figure 16:
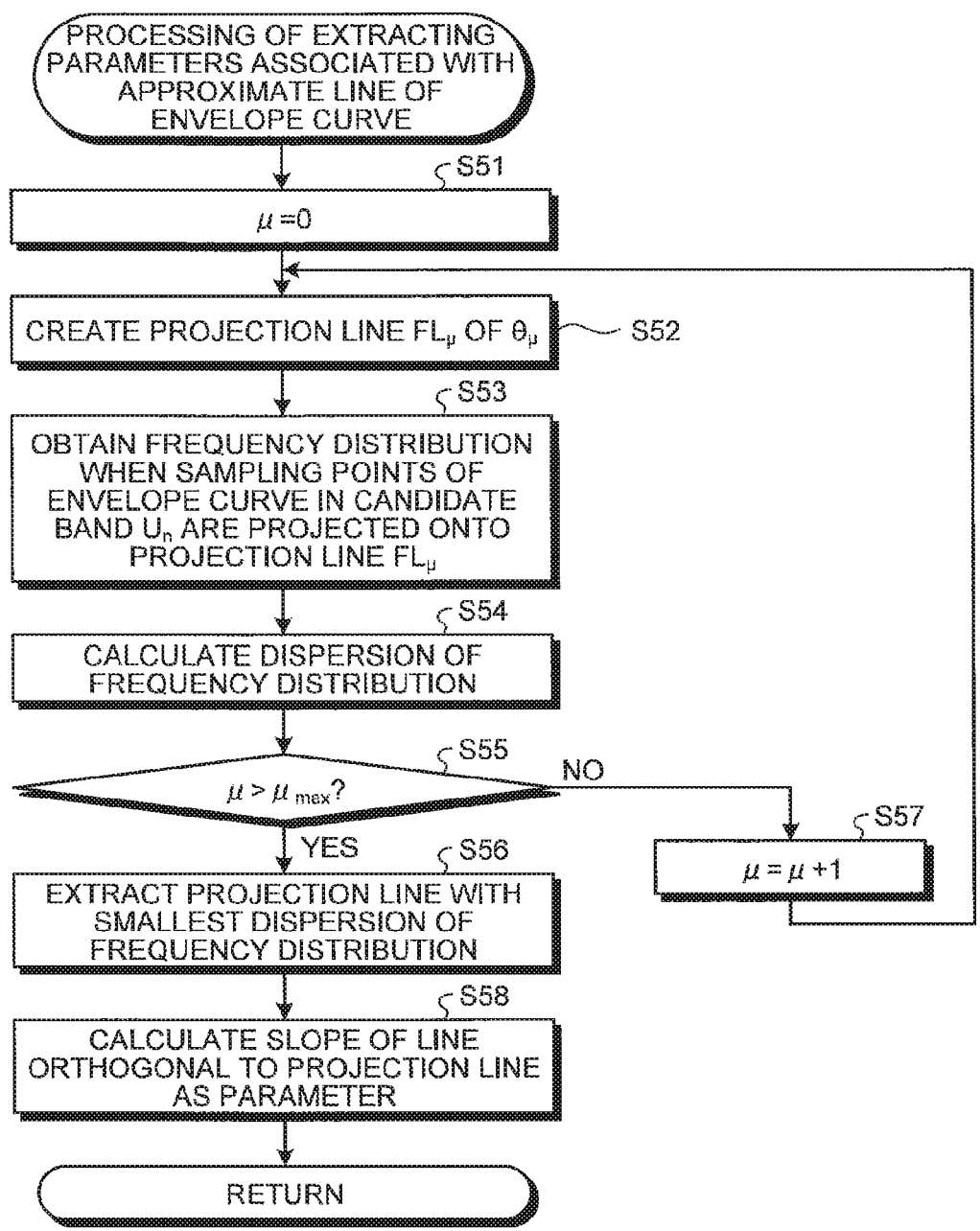
FIG. 16 is a flowchart illustrating an outline of a parameter extraction processing performed by the parameter extraction, unit in the ultrasound observation apparatus according to a second embodiment of the present invention.
Figure 17A:
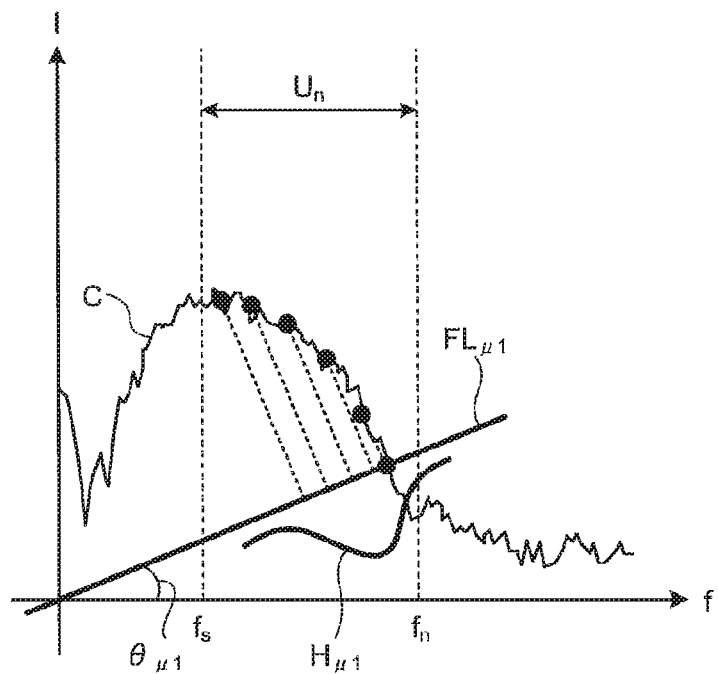
FIG. 17A is a diagram schematically illustrating an outline (first example) of a parameter extraction processing performed by the parameter extraction unit in the ultrasound observation apparatus according to the second embodiment of the present invention.
Figure 17B:
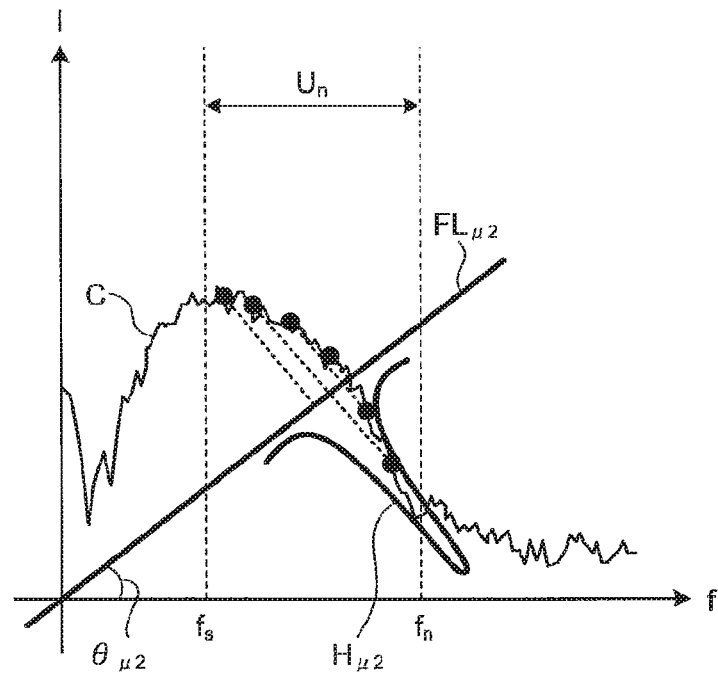
FIG. 17B is a diagram schematically illustrating an outline (second example) of a parameter extraction processing performed by the parameter extraction unit in the ultrasound observation apparatus according to the second embodiment of the present invention.

FIG. 16 is a flowchart illustrating an outline of the envelope curve parameter extraction processing (step S35 in FIG. 11) performed by the parameter extraction unit 333b according to the second embodiment. FIG. 17A and FIG. 17B are the diagrams schematically illustrating an outline of the parameter extraction processing performed by the parameter extraction unit 333b. The envelope curve parameter extraction processing will be described below with reference to FIGS. 16, 17A, and 17B.

At first, the parameter extraction unit 333b sets a counter μ for identifying a projection line at 0 (step S51).

The parameter extraction unit 333b creates a projection line with an angle parameter $\theta_\mu$ (step S52). The angle parameter $\theta_\mu$ is an angle associated with the slope of the projection line in the plane (horizontal axis: frequency f, vertical axis: intensity I) giving an envelope curve. In other words, the slope of the projection line is given as $\tan \theta_\mu$. FIG. 17A illustrates the projection line $FL_{\mu1}$ when the counter μ=μ1 (angle parameter $\theta_\mu = \theta_{\mu1}$) is established. Further, FIG. 17B illustrates the projection line $FL_{\mu2}$ when the counter μ=μ2 (angle parameter $\theta_\mu = \theta_{\mu2}$) is established. Herein, 0≤μ1 and μ2≤$\mu_{max}$ are met assuming μ1≠μ2 and the maximum value $\mu_{max}$ of the counter μ.

Subsequently, the parameter extraction unit 333b projects sampling points of the envelope curve C in the candidate band $U_n$ onto a projection line thereby to obtain a frequency distribution on the projection line (step S53). The curve $H_{\mu1}$ illustrated in FIG. 17A is a histogram corresponding to the frequency distribution obtained for the projection line $FL_{\mu1}$ by the parameter extraction unit 333b. The curve $H_{\mu2}$ illustrated in FIG. 17B is a histogram corresponding to the frequency distribution obtained for the projection line $FL_{\mu2}$ by the parameter extraction unit 333b.

Thereafter, the parameter extraction unit 333b calculates a dispersion of the frequency distribution obtained in step S53, and writes and stores it into the parameter information storage unit 372 (step S54).

Thereafter, the parameter extraction unit 333b determines whether the counter μ is larger than the maximum value $\mu_{max}$ (step S55). As a result of the determination, when μ>$\mu_{max}$ is established (step S55: Yes), the parameter extraction unit 333b proceeds to the processing in step S56. On the other hand, as a result of the determination, μ≤$\mu_{max}$ is established (step S55: No), the parameter extraction unit 333b increments the counter μ by 1 (step S57), and returns to the processing in step S52. Herein, the angle parameter increment Δθ is constant irrespective of μ when the parameter extraction unit 333b increments the counter μ by 1. The increment Δθ can be arbitrarily set, and may be set and input by the user via the input unit 35.

In step S56, the parameter extraction unit 333b extracts a projection line for which a dispersion giving a statistical variation of the frequency distribution is the smallest when the sampling points are projected with reference to the parameter information storage unit 372 (step S56). Subsequently, the parameter extraction unit 333b calculates the slope of a line orthogonal to the projection line extracted in step S56, and writes and stores the slope as the parameter $P_n$ of the envelope curve C into the parameter information storage unit 372 (step S58).

Figure 18:
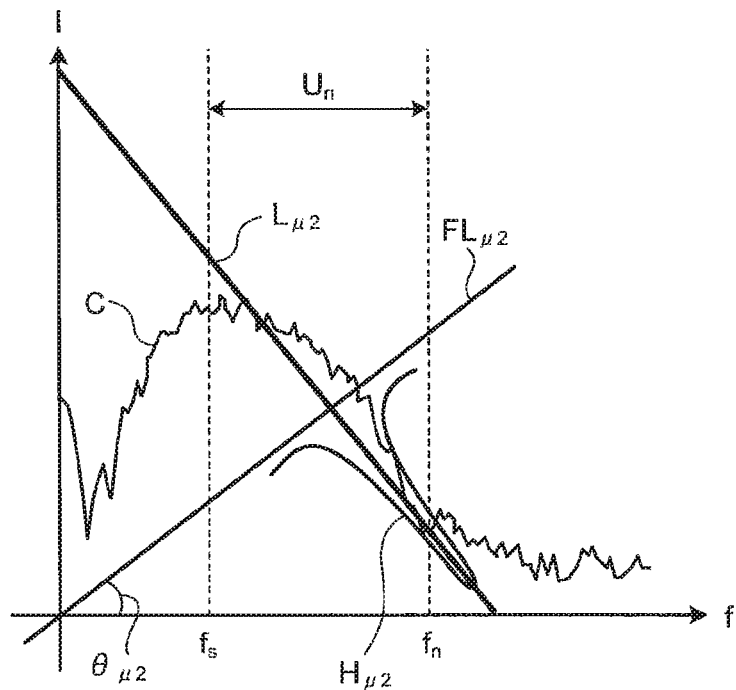
FIG. 18 is a diagram schematically illustrating a processing of calculating the slope of a line orthogonal to a projection line by the parameter extraction unit in the ultrasound observation apparatus according to the second embodiment of the present invention.

FIG. 18 is a diagram schematically illustrating the processing in step S58. FIG. 18 illustrates that a projection line for which the dispersion of a frequency distribution is the smallest is the projection line $FL_{\mu2}$. In this case, the parameter extraction unit 333b extracts the slope of the line $L_{\mu2}$ orthogonal to the projection line $FL_{\mu 2}$ as the parameter $P_n$. The slope of the line $L_{\mu 2}$ is expressed as $\tan(\theta_{\mu 2}+90°)$ by use of the angle parameter $\theta_{\mu 2}$.

According to the second embodiment of the present invention described above, as in the first embodiment, an optimum frequency band for analysis is adaptively determined when a frequency spectrum is approximated, and thus different tissue characteristics even at the same reception depth can be more obviously distinguished as compared with the conventional technique in which a frequency band is fixed at least per reception depth. Therefore, according to the second embodiment, it is possible to distinguish tissue characteristics of the observation target with a high degree of accuracy.

Further, also in the second embodiment, the parameters of an approximate line for approximating an envelope curve in a plurality of candidate bands are extracted, a variation between two parameters extracted in two candidate bands, for which the values of the bandwidths in the candidate bands are adjacent among the parameters extracted per candidate band, is calculated, and a frequency band is determined based on a change in the sign of the variation, thereby more finely setting a frequency band depending on tissue characteristics.

According to the second embodiment, the amount giving a statistical variation of a frequency distribution when sampling points within a candidate band are projected onto a projection line may take any of a standard deviation, a difference between the maximum value and the minimum value of a feature in a population, or a half width of a distribution of the features, for example. The reciprocal of a dispersion may be applied as the amount giving a statistical variation, but in this case, the parameters are of course determined by use of a projection line whose value is maximum.

Further, according to the second embodiment, the parameter extraction unit 333b may find a frequency distribution when sampling points are projected onto a plurality projection lines set in plane with an envelope curve, determine a projection line for which a statistical variation is the smallest in the found frequency distribution, and extract the intercept of a line orthogonal to the projection line and passing through the highest frequency point on the projection line as a parameter of the envelope curve. The line $L_{\mu 2}$ illustrated in FIG. 18 is a Line meeting the two conditions.

Further, according to the second embodiment, a projection line for calculating parameters may be set based on an index which is defined by use of a mode value of a histogram corresponding to a frequency distribution in addition to a statistical variation of the frequency distribution and which takes a larger value as the mode value is larger and takes a larger value as the statistical variation is smaller. Specifically, when a statistical variation is a dispersion, it is calculated per projection line with an index of (mode value)/(dispersion), and parameters of an envelope curve may be calculated by use of a projection line for which the value of the index is maximum.

Other Embodiments

The exemplary embodiments for carrying out the present invention have been described above, but the present invention is not limited to only the first and second embodiments described above. For example, the frequency band setting processing and the feature calculation processing may be performed after the attenuation correction is made on a frequency spectrum, for example. In this case, the attenuation correction processing may not be performed in the feature calculation processing.

Further, the present invention can be applied to ultrasound probes other than ultrasound endoscopes. An ultrasound miniature probe with a small diameter, which has no optical system, can be applied as an ultrasound probe. An ultrasound miniature probe is typically inserted into biliary tract, bile duct, pancreas duct, trachea, bronchi, urethra, or urinary duct to be used for observing its surrounding organs (such as pancreas, lung, prostate gland, bladder, and lymph nodes). Further, an external ultrasound probe for applying ultrasound waves from the surface of a subject may be applied as ultrasound probe. The external ultrasound probe is typically used for observing abdominal organs (liver, gallbladder, and bladder), breast (mammary gland in particular), and thyroid gland.

According to some embodiments, a frequency band used for calculating a feature of a frequency spectrum is set by use of parameters associated with a frequency spectrum in each of a plurality of candidate bands having different bandwidths, and a feature of each frequency spectrum is calculated based on the set frequency band. Hence, it is possible to adaptively determine an optimum frequency band for analysis in approximating the frequency spectrum, thereby to distinguish tissue characteristics of an observation target with a high degree of accuracy.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus for generating an ultrasound image based on an ultrasound signal obtained by an ultrasound probe, the ultrasound probe having an ultrasound transducer for transmitting an ultrasound wave to an observation target and receiving the ultrasound wave reflected from the observation target, the ultrasound observation apparatus comprising:
a processor comprising hardware, wherein the processor is configured to:
analyze a frequency of the ultrasound signal to calculate a plurality of frequency spectra depending on a reception depth and a reception direction of the ultrasound signal;
set a frequency band used for calculating a feature of each of the frequency spectra calculated by use of parameters associated with a frequency spectrum in each of a plurality of candidate bands having different bandwidths;
calculate the feature of each of the frequency spectra based on the frequency band set; and
generate feature image data for displaying information on the feature calculated,
wherein setting the frequency band comprises:
detecting an envelope curve of each of the frequency spectra;
extracting the parameters in the plurality of candidate bands, respectively, the parameters being associated with an approximate line obtained by approximating the envelope curve;
calculating a variation between two parameters respectively extracted in two candidate bands of the plurality of candidate bands having a predetermined relationship, among the parameters extracted per candidate band; and determining the frequency band based on the variation calculated, wherein extracting the parameters in the plurality of candidate bands comprises:

sequentially increasing a maximum value of a frequency in each candidate band while fixing a minimum value thereof thereby to set the plurality of candidate bands;

approximating the envelope curve by a line to extract a parameter each time one of the candidate bands is set; and outputting the parameter extracted, wherein if the processor already performs parameter extraction processing at least twice, the processor is configured to calculate, as the variation, a difference between a latest parameter and a parameter extracted in a previous parameter extraction processing, wherein if the processor already performs variation calculation processing at least twice, the processor is configured to compare a latest variation with a variation calculated in a previous variation calculation processing, and, if a sign of the variation changes from zero or one sign to the other sign as a result of comparison, the processor is configured to determine, as the frequency band, one of the candidate bands in extracting the parameter in the previous parameter extraction processing, and the processor is configured to repeatedly perform the parameter extraction processing, the variation calculation processing, and the comparison, respectively, until the processor determines the frequency band.

2. The ultrasound observation apparatus according to claim 1, wherein the processor is configured to perform a regression analysis on the envelope curve to calculate the line, and to determine a slope of the calculated line as the parameters.

3. The ultrasound observation apparatus according to claim 1, wherein the processor is configured to sequentially increase a maximum value of a frequency in each candidate band while fixing a minimum value thereof thereby to set the plurality of candidate bands, and to approximate the envelope curve by a line in each candidate band thereby to extract the parameters, wherein the processor is configured to calculate, as the variation, a difference between the two parameters respectively extracted in the two candidate bands whose bandwidths are adjacent, and wherein the processor is configured to calculate an approximate curve in which an absolute value of the variation is represented as a function of a maximum frequency in one of the two candidate bands whose bandwidth is smaller than that of the other of the two candidate bands, and to determine the frequency band based on the maximum frequency when the absolute value is minimum in the approximate curve.

4. The ultrasound observation apparatus according to claim 1, wherein the processor is configured to sequentially increase a maximum value of a frequency in each candidate band while fixing a minimum value thereof thereby to set the plurality of candidate bands, and to approximate the envelope curve by a line in each candidate band thereby to extract the parameters, wherein the processor is configured to calculate, as the variation, a difference between the two parameters respectively extracted in the two candidate bands whose bandwidths are adjacent, and wherein the processor is configured to calculate an approximate curve in which the variation is represented as a function of a maximum frequency in one of the two candidate bands whose bandwidth is smaller than that of the other of the two candidate bands, and to determine the frequency band based on the maximum frequency when a value of the variation is zero in the approximate curve.

5. The ultrasound observation apparatus according to claim 1, wherein the processor is configured to calculate a frequency distribution in each of a plurality of projection lines when sampling points on the envelope curve in each candidate band are projected onto the plurality of projection lines, wherein the processor is configured to calculate a slope of the line based on one of the projection lines whose statistical dispersion in the frequency distribution is the smallest, and wherein the processor is configured to determine the calculated slope of the line as the parameters.

6. The ultrasound observation apparatus according to claim 1, wherein the processor is configured to calculate a frequency distribution in each of a plurality of projection lines when sampling points on the envelope curve in each candidate band are projected onto the plurality of projection lines, wherein the processor is configured to select a projection line among the plurality of projection lines that is used for calculating a slope of the line, based on an index which is defined by use of a mode value and a statistical dispersion in the frequency distribution and takes a larger value as the mode value is larger and takes a larger value as the statistical dispersion is smaller, wherein the processor is configured to calculate the slope of the line based on the selected projection line, and wherein the processor is configured to determine the calculated slope of the line as the parameters.

7. The ultrasound observation apparatus according to claim 1, wherein the processor is configured to approximate the envelope curve in the frequency band by a regression analysis, and then to perform an attenuation correction for reducing a contribution of attenuation occurring when the ultrasound wave propagates, thereby to calculate the feature of each of the frequency spectra.

8. A method for operating an ultrasound observation apparatus that is configured to generate an ultrasound image based on an ultrasound signal obtained by an ultrasound probe, the ultrasound probe having an ultrasound transducer for transmitting an ultrasound wave to an observation target and receiving the ultrasound wave reflected from the observation target, the method comprising:

by a processor comprising hardware, analyzing a frequency of the ultrasound signal to calculate a plurality of frequency spectra depending on a reception depth and a reception direction of the ultrasound signal;

by the processor, setting a frequency band used for calculating a feature of each of the frequency spectra by use of parameters associated with a frequency spectrum in each of a plurality of candidate bands having different bandwidths;

by the processor, calculating the feature of each of the frequency spectra based on the frequency band; and by the processor, generating feature image data based on the feature, wherein setting of the frequency band comprises:

by the processor, detecting an envelope curve of each of the frequency spectra;

by the processor, extracting the parameters in the plurality of candidate bands, respectively, the parameters being associated with an approximate line obtained by approximating the envelope curve;

by the processor, calculating a variation between two parameters respectively extracted in two candidate bands of the plurality of candidate bands having a predetermined relationship, among the parameters extracted per candidate band; and by the processor, determining the frequency band based on the variation, wherein extracting the parameters in the plurality of candidate bands comprises:

by the processor, sequentially increasing a maximum value of a frequency in each candidate band while fixing a minimum value thereof thereby to set the plurality of candidate bands;

by the processor, approximating the envelope curve by a line to extract a parameter each time one of the candidate bands is set; and by the processor, outputting the parameter extracted, wherein if parameter extraction processing is performed at least twice, calculating, by the processor, as the variation, a difference between a latest parameter and a parameter extracted in a previous parameter extraction processing, wherein if variation calculation processing is performed at least twice, comparing, by the processor, a latest variation with a variation calculated in a previous variation calculation processing, and, if a sign of the variation changes from zero or one sign to the other sign as a result of comparison, determining, by the processor, as the frequency band, one of the candidate bands in extracting the parameter in the previous parameter extraction processing, and repeatedly performing, by the processor, the parameter extraction processing, the variation calculation processing, and the comparison, respectively, until the frequency band is determined by the processor.

9. A non-transitory computer-readable recording medium with an executable program stored thereon, the program causing an ultrasound observation apparatus that is configured to generate an ultrasound image based on an ultrasound signal obtained by an ultrasound probe, the ultrasound probe having an ultrasound transducer for transmitting an ultrasound wave to an observation target and receiving the ultrasound wave reflected from the observation target, to execute:

by a processor comprising hardware, analyzing a frequency of the ultrasound signal to calculate a plurality of frequency spectra depending on a reception depth and a reception direction of the ultrasound signal;

by the processor, setting a frequency band used for calculating a feature of each of the frequency spectra by use of parameters associated with a frequency spectrum in each of a plurality of candidate bands having different bandwidths;

by the processor, calculating the feature of each of the frequency spectra based on the frequency band; and by the processor, generating feature image data based on the feature, wherein setting of the frequency band comprises:

by the processor, detecting an envelope curve of each of the frequency spectra;

by the processor, extracting the parameters in the plurality of candidate bands, respectively, the parameters being associated with an approximate line obtained by approximating the envelope curve;

by the processor, calculating a variation between two parameters respectively extracted in two candidate bands of the plurality of candidate bands having a predetermined relationship, among the parameters extracted per candidate band; and by the processor, determining the frequency band based on the variation, wherein extracting the parameters in the plurality of candidate bands comprises:

by the processor, sequentially increasing a maximum value of a frequency in each candidate band while fixing a minimum value thereof thereby to set the plurality of candidate bands;

by the processor, approximating the envelope curve by a line to extract a parameter each time one of the candidate bands is set; and by the processor, outputting the parameter extracted, wherein if parameter extraction processing is performed at least twice, calculating, by the processor, as the variation, a difference between a latest parameter and a parameter extracted in a previous parameter extraction processing, wherein if variation calculation processing is performed at least twice, comparing, by the processor, a latest variation with a variation calculated in a previous variation calculation processing, and, if a sign of the variation changes from zero or one sign to the other sign as a result of comparison, determining, by the processor, as the frequency band, one of the candidate bands in extracting the parameter in the previous parameter extraction processing, and repeatedly performing, by the processor, the parameter extraction processing, the variation calculation processing, and the comparison, respectively, until the frequency band is determined by the processor.

* * * * *